United States Patent
Hopenfeld et al.

(10) Patent No.: US 9,192,309 B1
(45) Date of Patent: Nov. 24, 2015

(54) ACUTE ISCHEMIA DETECTION BASED ON SMOOTHED TEMPORAL THRESHOLDING

(71) Applicant: ANGEL MEDICAL SYSTEMS, INC., Fair Haven, NJ (US)

(72) Inventors: Bruce Hopenfeld, Salt Lake City, UT (US); Steven R. Johnson, Fair Haven, NJ (US)

(73) Assignee: Angel Medical Systems, Inc., Fair Haven, NJ (US)

( * ) Notice: Subject to any disclaimer, the term of this patent is extended or adjusted under 35 U.S.C. 154(b) by 0 days.

(21) Appl. No.: 14/591,268

(22) Filed: Jan. 7, 2015

Related U.S. Application Data

(63) Continuation of application No. 14/170,894, filed on Feb. 3, 2014, now Pat. No. 8,954,139, and a continuation-in-part of application No. 13/788,143, filed on Mar. 7, 2013, now Pat. No. 8,682,422, and a continuation of application No. 12/868,308, filed on Aug. 25, 2010, now Pat. No. 8,428,703.

(51) Int. Cl.
*A61B 5/0452* (2006.01)
*A61B 5/02* (2006.01)

(52) U.S. Cl.
CPC ........... *A61B 5/02028* (2013.01); *A61B 5/0452* (2013.01)

(58) Field of Classification Search
CPC .. A61B 5/0452; A61B 5/0006; A61B 5/0031; A61B 5/02405; A61B 5/02455; A61B 5/04012; A61B 5/042; A61B 5/0432; A61B 5/044; A61B 5/0472; A61B 5/413; A61B 5/686; A61B 5/7264; A61B 5/746
See application file for complete search history.

(56) References Cited

U.S. PATENT DOCUMENTS

| | | |
|---|---|---|
| 5,792,047 A | 8/1998 | Coggins |
| 6,217,525 B1 | 4/2001 | Medema et al. |
| 6,324,421 B1 | 11/2001 | Stadler et al. |
| 6,609,023 B1 | 8/2003 | Fischell et al. |
| 6,972,938 B2 | 12/2005 | Hiraga |
| 7,512,438 B2 | 3/2009 | Fischell et al. |
| 7,930,017 B1 | 4/2011 | Fain et al. |
| 2004/0215092 A1 | 10/2004 | Fischell et al. |
| 2005/0137483 A1 | 6/2005 | Fischell et al. |
| 2008/0188763 A1 | 8/2008 | John et al. |
| 2009/0082682 A1 | 3/2009 | Fischell et al. |
| 2009/0192397 A1 | 7/2009 | Fischell et al. |
| 2009/0216141 A1 | 8/2009 | Fischell et al. |

(Continued)

OTHER PUBLICATIONS

Pueyo, et al., "High-frequency signature of the QRS complex across ischemia quantified by QRS slopes." Computers in Cardiology, Sep. 25-28, 2005, pp. 659-662.

(Continued)

*Primary Examiner* — Rex R Holmes
(74) *Attorney, Agent, or Firm* — Rosenberg, Klein & Lee

(57) ABSTRACT

A heart monitor is disclosed. The monitor computes ST segment deviations and stores the results in heart rate based histograms. Periodically, the monitor analyzes the histogram data to determine a normal range of ST deviation for a particular heart rate range. The monitor computes heart rate dependent ischemia detection thresholds based on the upper and lower boundaries of the normal range. A current threshold for a heart rate range is set as a weighted average of the prior threshold and a provisional threshold based on recent data, thereby limiting the amount the actual detection threshold changes from period to period.

9 Claims, 23 Drawing Sheets

(56) References Cited

U.S. PATENT DOCUMENTS

2011/0040199 A1    2/2011   Hopenfeld
2011/0245699 A1*  10/2011   Snell et al. .................... 600/509

OTHER PUBLICATIONS

Jager, et al.; "Detection of transient ST segment episodes during ambulatory ECG monitoring." Computers and Biomedical Research, 1998 vol. 31(5), pp. 305-322.

* cited by examiner

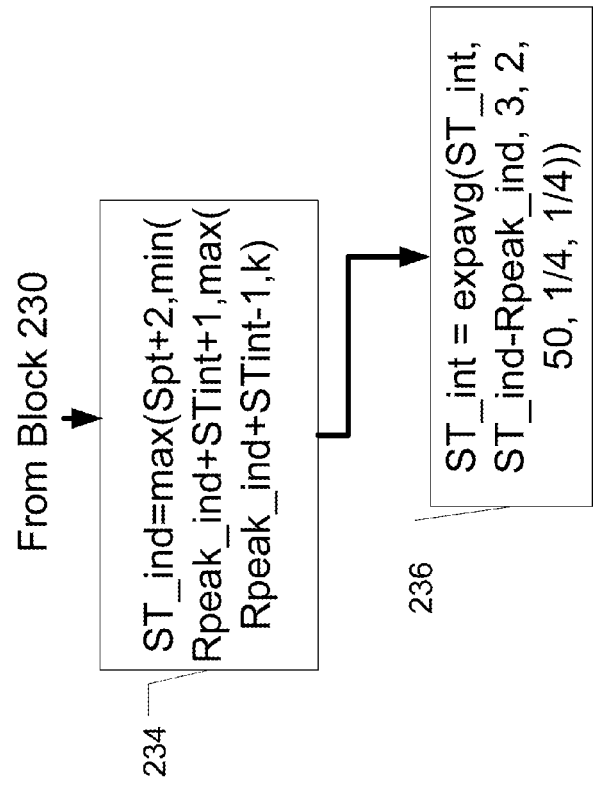

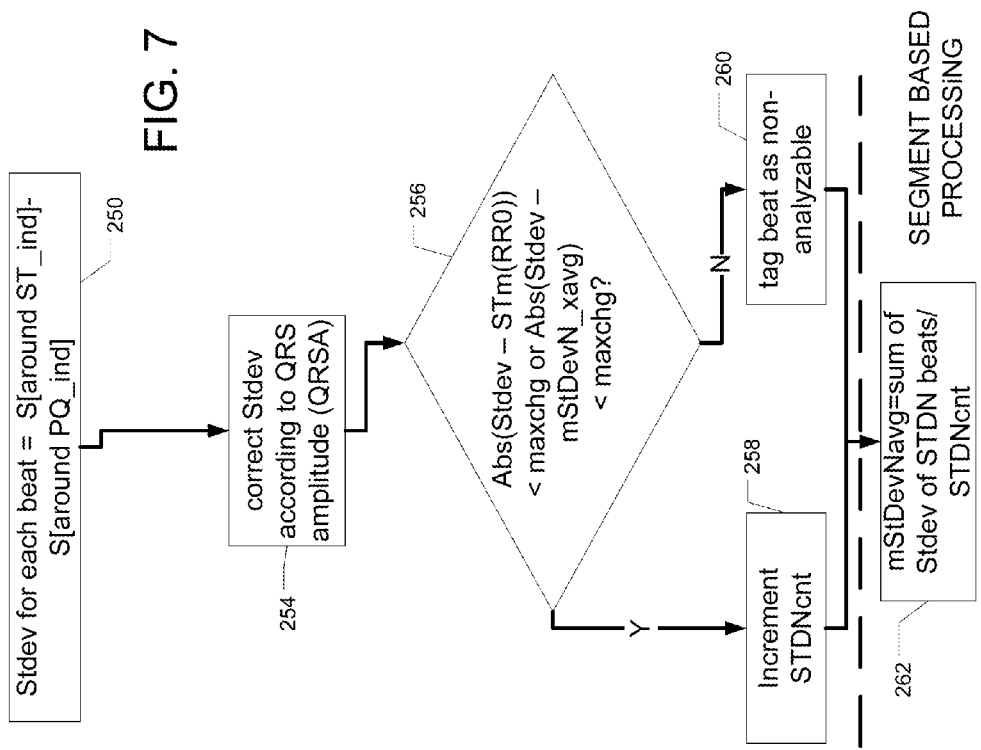

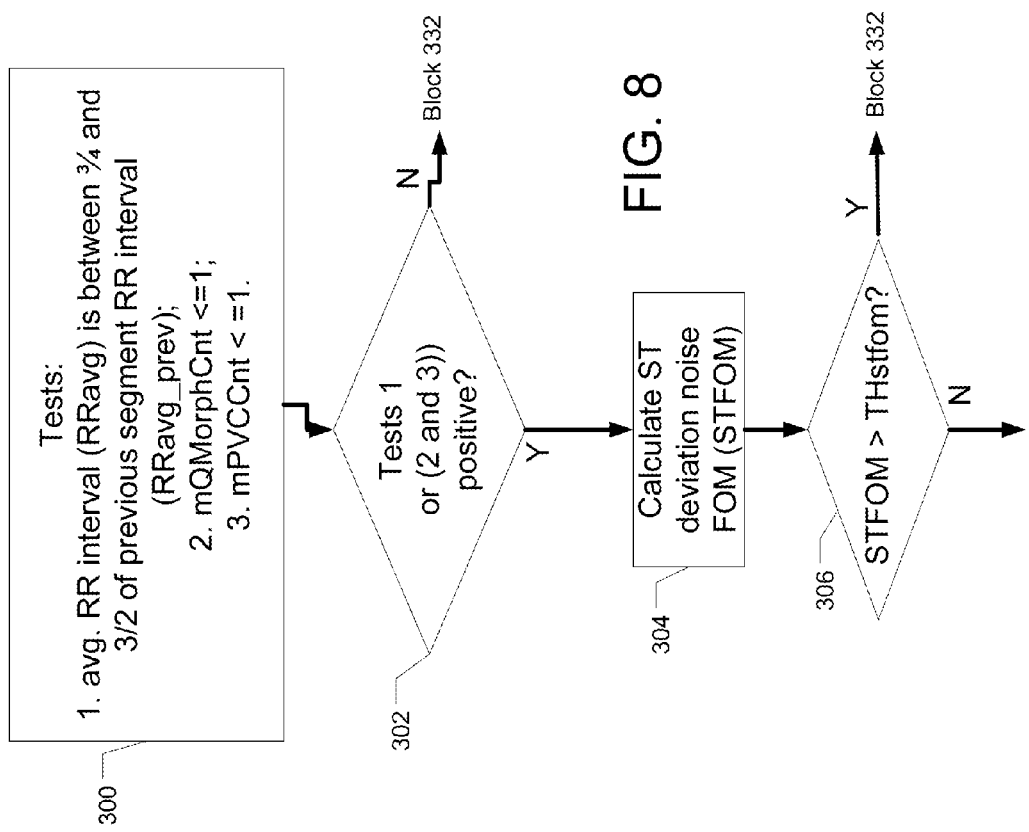

FIG. 15

| ST states of the left and leftup leads | Classifier | Threshold |
|---|---|---|
| Left lead > median; Leftup lead > median | $(ST_{left} - STMX\_{left})/(THP_{left} - STMX\_{left}) + (ST_{leftup} - STMX\_{leftup})/(THP_{leftup} - STMX_{leftup})$ | 1.3 |
| Left lead > median; Leftup lead < median | $(ST_{left} - STMX\_{left})/(THP_{left} - STMX\_{left}) + (ST_{leftup} - STMN\_{leftup})/(THN_{leftup} - STMN_{leftup})$ | 1.3 |
| Left lead < median; Leftup lead > median | $(ST_{left} - STMN\_{left})/(THN_{left} - STMN\_{left}) + (ST_{leftup} - STMX\_{leftup})/(THP_{leftup} - STMX_{leftup})$ | 1.3 |
| Left lead < median; Leftup lead < median | $(ST_{left} - STMN\_{left})/(THN_{left} - STMN\_{left}) + (ST_{leftup} - STMN\_{leftup})/(THN_{leftup} - STMN_{leftup})$ | 1.3 |

ACUTE ISCHEMIA DETECTION BASED ON SMOOTHED TEMPORAL THRESHOLDING

REFERENCE TO RELATED APPLICATIONS

This application is being filed as a Continuation application of Ser. No. 14/170,894, filed 3 Feb. 2014, currently pending, which is a Continuation-in-Part of Ser. No. 13/788, 143, filed on 7 Mar. 2013, now U.S. Pat. No. 8,682,422, which is a Continuation of Ser. No. 12/868,308, filed on 25 Aug. 2010, now U.S. Pat. No. 8,428,703.

GOVERNMENT FUNDING

This invention was made with support under grant 1R43HL096158-01 awarded by the National Heart, Lung and Blood Institute of the National Institutes of Health. The United States government has certain rights in the invention.

FIELD OF USE

This invention is in the field of medical device systems that monitor a patient's cardiovascular condition.

BACKGROUND OF THE INVENTION

Heart disease is the leading cause of death in the United States. A heart attack, also known as an acute myocardial infarction (AMI), typically results from a blood clot or "thrombus" that obstructs blood flow in one or more coronary arteries. AMI is a common and life-threatening complication of coronary artery disease. Coronary ischemia is caused by an insufficiency of oxygen to the heart muscle. Ischemia is typically provoked by physical activity or other causes of increased heart rate when one or more of the coronary arteries is narrowed by atherosclerosis. AMI, which is typically the result of a completely blocked coronary artery, is the most extreme form of ischemia. Patients will often (but not always) become aware of chest discomfort, known as "angina", when the heart muscle is experiencing ischemia. Those with coronary atherosclerosis are at higher risk for AMI if the plaque becomes further obstructed by thrombus.

Detection of AMI often involves analyzing changes in a person's ST segment voltage. A common scheme for computing changes in the ST segment involves determining a quantity known as ST deviation for each beat. ST deviation is the value of the electrocardiogram at a point or points during the ST segment relative to the value of the electrocardiogram at some point or points during the PQ segment. Whether or not a particular ST deviation is indicative of AMI depends on a comparison of that ST deviation with a threshold.

The threshold may be absolute (e.g. 0.2 mV) or relative to a person's own ST deviation statistics, as disclosed in U.S. patent application Ser. No. 10/642,345, invented by Fischell et. al., owned by the assignee hereof, filed August 2003, and U.S. patent application Ser. No. 12/461,442, invented by Hopenfeld, filed August 2009, owned by the assignee hereof. Despite this work, there is still a need for an effective system for setting patient specific thresholds for the detection of cardiac events.

SUMMARY OF THE INVENTION

An embodiment of the present invention comprises a heart monitor that may be chronically implanted or external. The device, which includes an analog to digital convertor and a processor that performs beat detection, monitors the time course of a heart signal parameter, namely ST segment deviation, computed from an electrocardiogram. An ST deviation time series is generated by a recursive filter that is preferably an exponential average filter whose output is a weighted sum of the then existing ST time series value and current ST deviation values of analyzable beats. A heart rate value is analogously computed for each ST deviation value in the time series.

Information pertaining to the ST deviations is stored in histogram format according to heart rate so as to preserve characteristics of the statistical distribution of ST deviation as a function of heart rate. Periodically, the monitor analyzes the histogram data to determine a normal range of ST deviation for a particular heart rate range. The monitor computes heart rate dependent ischemia detection thresholds based on the upper and lower boundaries of the normal range. In some instances, the thresholds are set at specified distances from the boundaries, where the distances are functions of the dispersion of the ST deviation data for a particular heart rate range.

BRIEF DESCRIPTION OF THE DRAWINGS

FIGS. 6A and 6B are a flow chart of the preferred embodiment for determining the location of PQ and ST points.

FIG. 7 is a flowchart that shows steps for determining a measure of segment based ST deviation.

FIG. 8 is a flow chart of a routine that analyzes a segment's ST deviation values and other segment characteristics to determine whether the segment's average ST deviation should contribute to long term Filtered measures of ST deviation, ischemia diction, and long term ST/RR histograms.

FIG. 15 is a table describing ischemia detection thresholds based on the combination of ST segment information from two leads.

DETAILED DESCRIPTION OF THE INVENTION

Architecture

Figure 1:
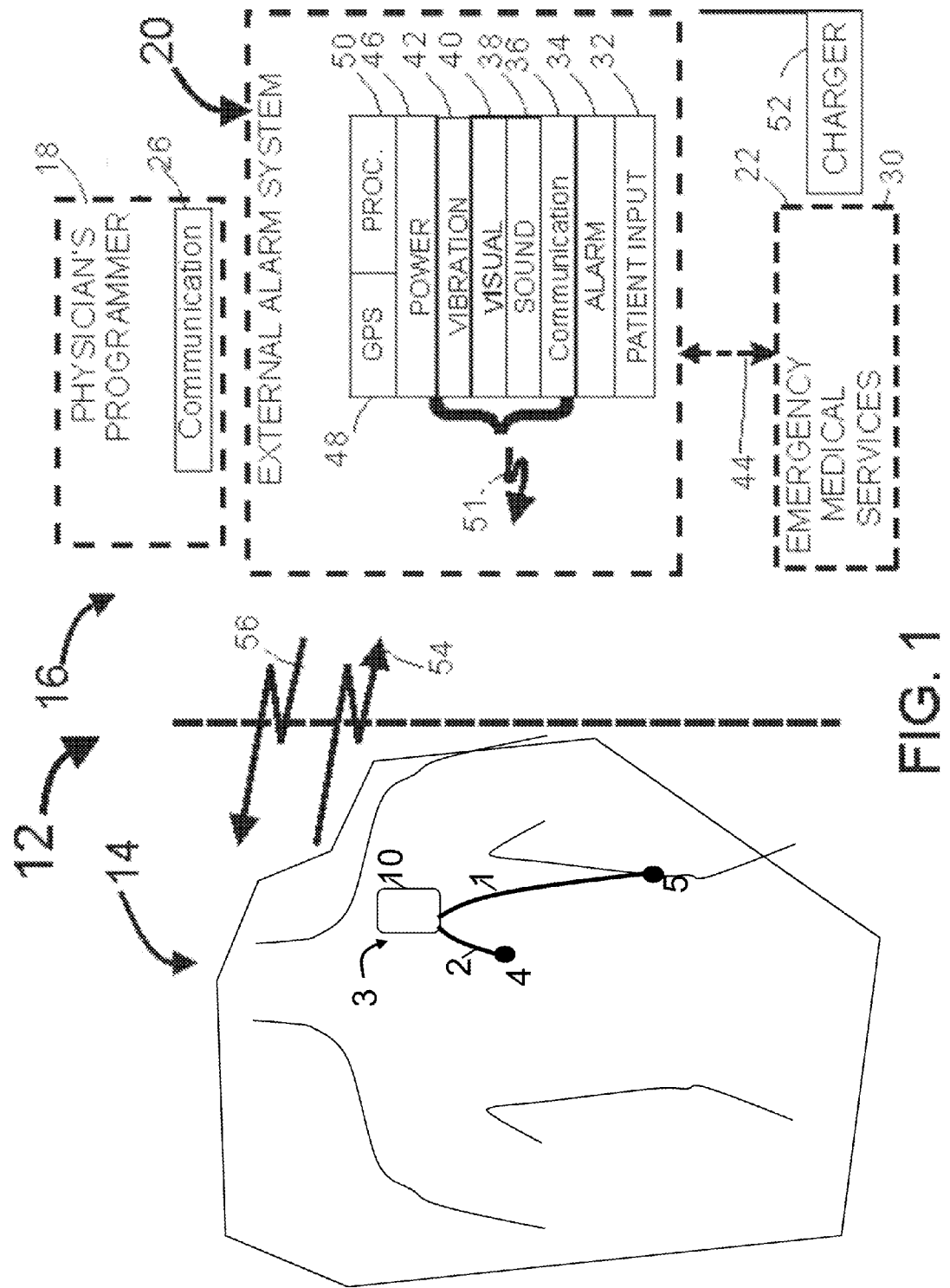
FIG. 1 illustrates a system for the detection of a cardiac event and for warning the patient that a medically relevant cardiac event is occurring.

FIG. 1 illustrates an example of a medical system 12 including implanted components 14 and external equipment 16. An implantable medical device (IMD) 3 includes sensors to monitor a cardiac condition associated with a patient. In one embodiment, sensors include electrodes 4 and 5 incorporated into insulated electrical wire leads 2 and 1, respectively, that are preferably placed subcutaneously. The leads 2 and 1 are electrically connected to the IMD 3, which comprises a case 10 that serves as a reference potential. Thus, the IMD 3 can obtain three bipolar voltage signals: between the electrode 4 and the case 10, between the electrode 5 and the case 10, and between electrodes 4 and 5.

FIG. 1 also shows external equipment 16, designed to communicate with the IMD 3, that includes: 1. a physician's programmer 18; 2. an external alarm system (EXD) 20 which may be implemented as one or more of: a pager-type device, a cell phone or PDA type device or a desktop unit; and, 3. a remote monitoring center 22. The physician's programmer 18 has 2-way wireless communication 26 for communication between the programmer 18, the IMD 3 and the EXD 20. The EXD 20 includes a communication module 36 having one or more antenna for wireless communication with the IMD 3, physician's programmer 18 and remote monitoring center 22. The physician's programmer 18 provides users with the capability of interacting with the IMD 3. The EXD 20 also provides external alarm signals for alerting a patient and allows two way wired or wireless communications with the remote monitoring center 22. The remote monitoring center 22 can be one or more third parties including a monitoring service, the patient's doctor, or other intended target.

The programmer 18 shown in FIG. 1 can be used to communicate with the IMD 3 in order to adjust operational parameters and to retrieve data from the IMD 3. Communication can include wireless signals 56 sent from the programmer 18 communications module 26 to the IMD 3 and incoming wireless signals 54 sent from the IMD 3 to the communications module 26 of the programmer 18.

In FIG. 1, the EXD 20 has a patient input module 32 which contains a series of physical controls such a buttons. A "patient initiate" button can allow for the initiation of communication between the EXD 20 and the IMD 3. An "alarm disable" button can be used to cause an alarm of the IMD 3 and/or EXD 20 to halt rather than repetitively and needlessly re-alerting a patient. A "panic" button can allow a patient to send an alarm with or without attached data from the IMD 3 to a remote monitoring center 22, even in the absence of IMD 3 or EXD 20 alarm notification. An "event" button can allow patients to tag events and thereby cause data to be tagged and/or sent remotely. An alarm module 34 can operate the communication module 36, sound module 38, visual module 40, and vibration module 42, to create an alarm signal 51 that comprises at least one of: communicating with a $3^{rd}$ party, a sonic alarm, a visual alarm, and a vibration alarm, respectively.

The communication module 36, with the one or more antennae, provides near-field and far-field wireless communication. The near-field communication may use inductively coupled wake-up type communication methods such as are well known, while medium and far-field communication may rely upon other means. The communication module 36 can employ standardized wireless methods such as Bluetooth, WiFi, the FCC medical band, and/or cellular communications system such as GSM, CDMA, TDMA. The communication module 36 allows for data and/or voice transmission to and from the medical monitoring center 22 via a communication link 44, and also allows communication with the IMD 3 and programmer 18. The sound module 38 has both sound input and output such as a microphone, and speaker, respectively and associated electronics for providing two-way voice communication with the remote monitoring center 22. Examples of external auditory alarm signals 51 include a periodic buzzing, a sequence of tones and/or speech which may be a pre-recorded message that instructs the patient as to what is happening and what actions should be taken or which may be real speech communicated by the remote monitoring center 22. The visual module 40 can include one or more colored diodes which are activated continuously, periodically, or according to a pattern that is associated with a particular alarm type. The visual module 40 may also include a display screen for displaying waveforms, pictures, and text related to system parameters, alarm information, or other information. The vibration module 42 can contain a vibration motor to produce the vibration alarm signal component of the alarm signal 51, and can also contain an accelerometer which can be used to test the vibration alarm and also to measure a patient's physical activity level when the EXD 20 is worn by the patient.

A processing module 50 of the EXD 20 contains a real time clock or timer and other components included within portable smart-devices and pagers. Further, in a preferred embodiment, the EXD 20 is realized using a smart-phone (e.g., an iPhone, Blackberry or Palm), which may, if necessary, be implemented using specialized software and/or smartcards including means for wireless communication with the IMD 3. The alarm module 34, as well as the other modules of the EXD 20, may be implemented in hardware or software, and contains all of the necessary components to implement alarming of the patient and/or remote station. The alarm module 34 collaborates with the processor module 50 to provide alerting by providing instructions to the processor or by receiving commands from the processor which cause it to implement alerting as defined in the alarm protocols, or both.

If an alarm notification is sent from the IMD 3 to the EXD 20, then the alarm module 34 can alert the patient, alert a $3^{rd}$ party, or no alarm may be provided and the EXD 20 is simply operated to send data to a 3rd party for evaluation or storage. When the detection of a life threatening event (e.g., AMI or arrhythmia) is the cause of the alarm, the EXD 20 could automatically notify remote monitoring center 22 that a serious event has occurred.

If communication with remote monitoring center 22 occurs, then the message sent over the link 44 may include at least one of the following types of information as previously stored in the memory provided within the EXD's processor module 50 or as directly uploaded from the IMD 3: (1) What type of medical event has occurred, (2) the patient's name, address and a brief medical history, (3) data provided by a GPS module 48, the data including GPS coordinates and/or directions to the patient's location; (4) patient data, historical monitoring data, and the data that caused the alarm and (5) continuous real time data as it is collected after the alarm. The EXD 20 may be charged with a charger 52 to charge a rechargeable power supply 46 in the EXD 20.

Figure 2:
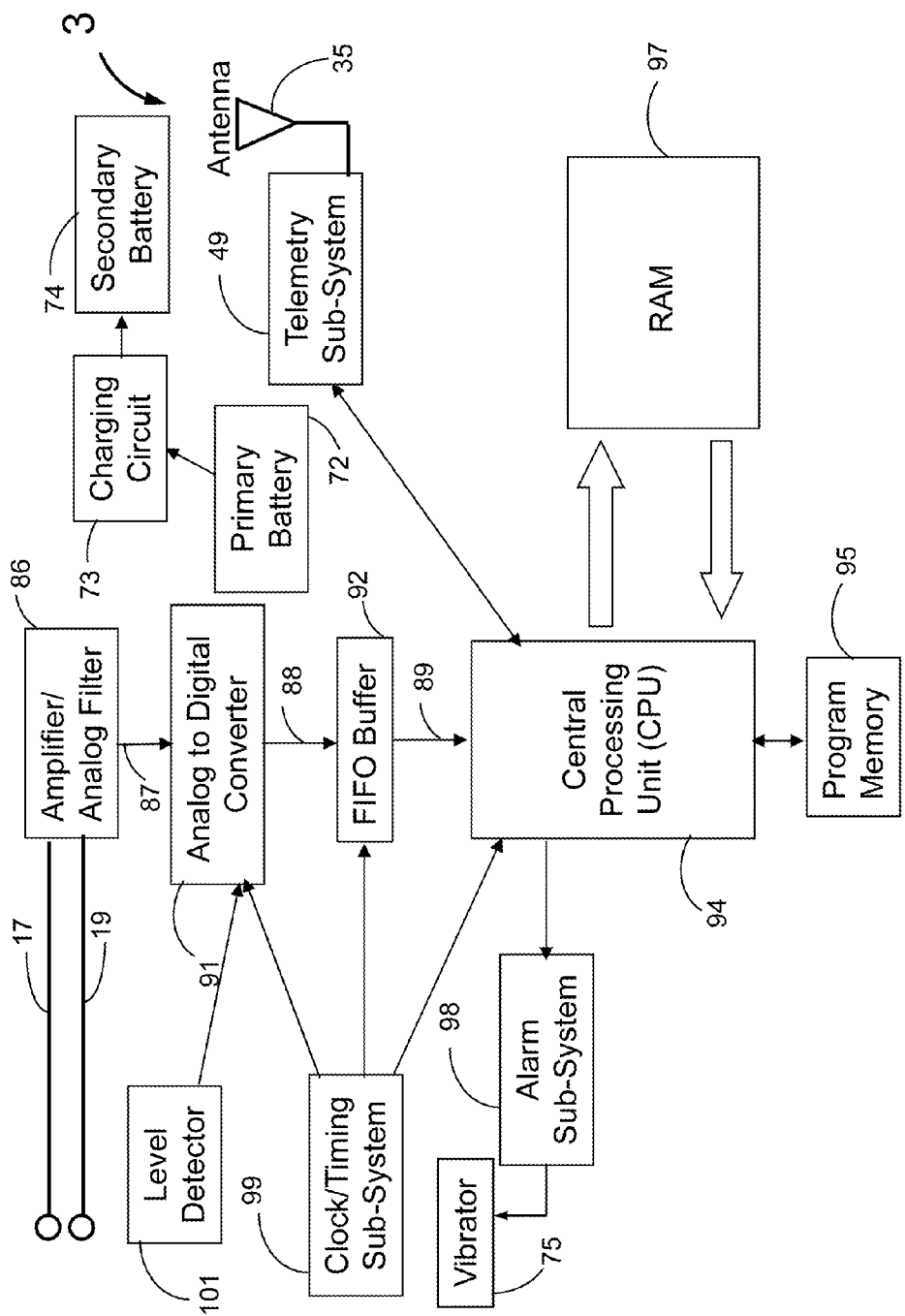
FIG. 2 is a block diagram of an implanted cardiac diagnostic system according to the present invention.

FIG. 2 is a block diagram of the IMD 3 with primary battery 72 and a secondary battery 74. The secondary battery 74 is typically a rechargeable battery of smaller capacity but higher current or voltage output than the primary battery 72 and is used for short term high output components of the IMD 3 like the RF chipset in a telemetry sub-system 49 or a vibrator 75 attached to an alarm sub-system 98. According to a dual battery configuration, the primary battery 72 will charge the secondary battery 74 through a charging circuit 73. The primary battery 72 is typically a larger capacity battery than the secondary battery 74. The primary battery 72 also typically has a lower self discharge rate as a percentage of its capacity than the secondary battery 74. It is also envisioned that the secondary battery could be charged from an external induction coil by the patient or by the doctor during a periodic check-up.

A bipolar signal (e.g. reflecting the potential difference between electrodes 4 and 5 shown in FIG. 1) is fed over wires 17 and 19 to an amplifier/analog filter 86. The amplifier/analog filter 86 amplifies the bipolar signal and filters the signal with a bandpass between 0.25 Hz and 50 Hz, resulting in a conditioned analog signal 87. The conditioned signal 87 is then converted to a digital signal 88 by an analog-to-digital converter 91, which preferably samples at a rate of 200 Hz. The digital signal 88 is buffered in a First-In-First-Out (FIFO) memory 92 and is digitally filtered with a filter whose transfer function is the inverse of the high pass transfer function of the amplifier/analog filter 86. Further details regarding this type of inverse digital filtering are found in EEG Handbook (revised series, Vol. 3), 1988, Chapter 2, Section 2.3.5.7.

For ease of description, only one bipolar signal is shown in FIG. 2. In the preferred embodiment, two bipolar signals are processed, and a third bipolar signal is derived by subtracting the digitized versions of the two bipolar signals. Furthermore, the two bipolar signals are preferably acquired simultaneously, so that fiducial points (e.g. an ST point, as will be described with reference to FIGS. 6A and 6B determined for one signal, preferably the signal corresponding to the voltage between electrodes 4 and 5, may be applied to the other bipolar signals (i.e., the electrode 4 referenced to the case 10 and the electrode 5 referenced to the case 10.)

A central processing unit (CPU) 94 is coupled to the FIFO memory 92. The CPU 94 is further coupled to a Random Access Memory (RAM) 97 and a program memory 95 that stores instructions that implement the methods described with reference to FIGS. 3-13. The CPU 94 performs the digital filtering described above.

A level detector/accelerometer 101 is coupled to the analog to digital converter 91. The level detector 101 detects whether a patient's torso is upright or supine and also, if the torso is supine, the extent of its rotation with respect to the earth (e.g. patient is lying flat on his/her back, lying on his/her right side or left side.) Many MEMS based level detectors can also operationally serve as inclinometers, accelerometers, and general detectors for motion/force exist.

Additional sensors may communicate with the IMD 3 wirelessly through the telemetry sub-system 49. The data from these leads may correspond to digitized electrocardiogram signals (that have been processed by a remote subcutaneous device).

The operation of most of the components in FIG. 2 is further described in U.S. patent application publication number 2004/0215092.

In a preferred embodiment of the present invention, the RAM 97 includes specific memory locations for 4 sets of electrocardiogram segment storage, including recent electrocardiogram storage, working memory for performing programming operations, memory for storing programming parameters that may be updated, and patient specific information (e.g. patient name, date of birth).

The telemetry sub-system 49 with an antenna 35 provides the IMD 3 the means for two-way wireless communication to and from the external equipment 16 of FIG. 1. Existing radiofrequency transceiver chip sets such as the Ash transceiver hybrids produced by RF Microdevices, Inc. can readily provide such two-way wireless communication over a range of up to 10 meters from the patient. It is also envisioned that short range telemetry such as that typically used in pacemakers and defibrillators could also be applied to the IMD 3. It is also envisioned that standard wireless protocols such as Bluetooth and 802.11a or 802.11b might be used to allow communication with a wider group of peripheral devices.

Flowcharts

Figure 3:
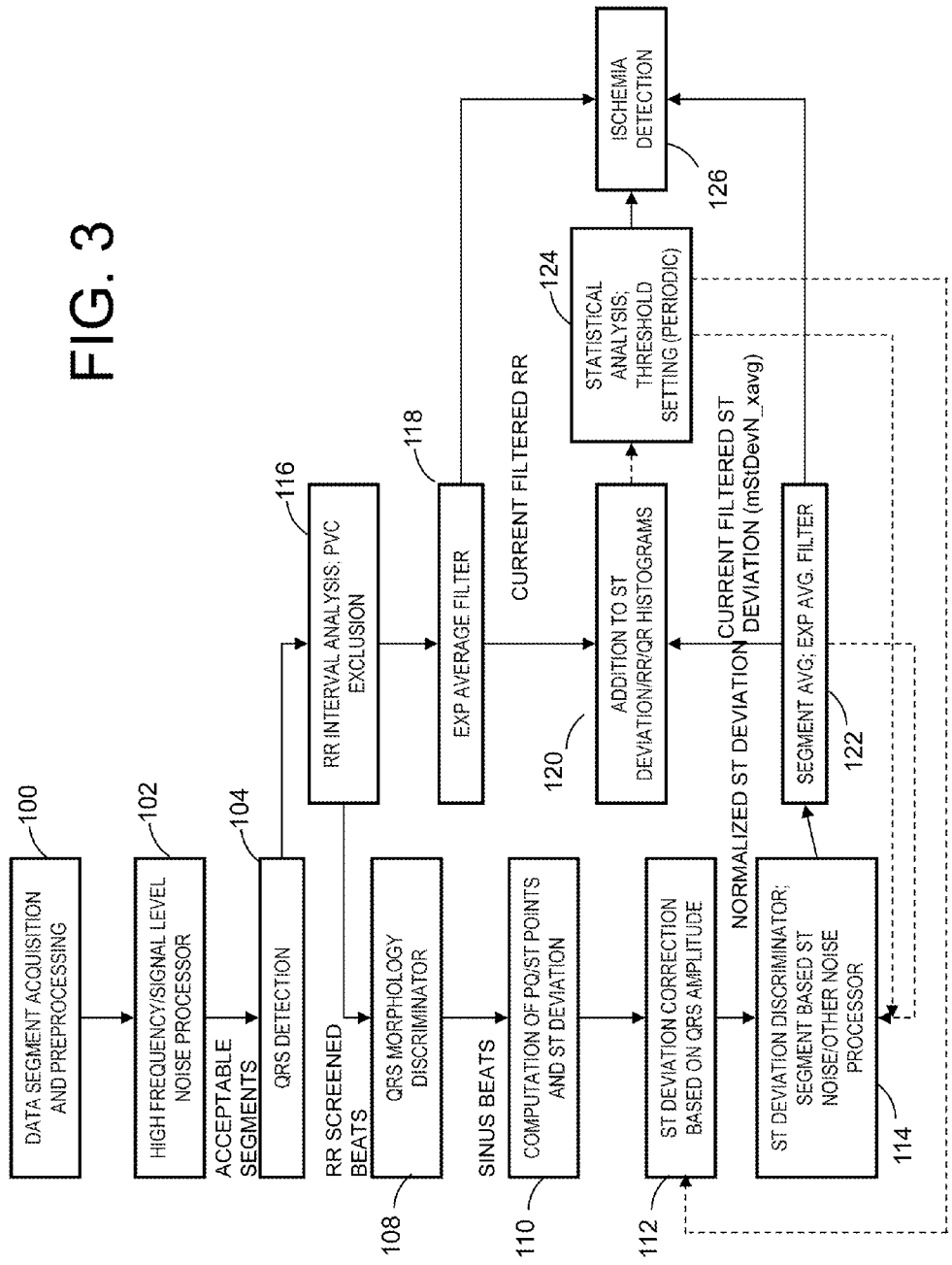
FIG. 3 is a high level flow chart of a method for detecting ischemia.

FIG. 3 is a high level flow chart of a method for detecting cardiac ischemia. The method involves processing 10 second long data segments collected by the IMD 3 once every ninety seconds in normal conditions. The segment acquisition rate is preferably increased to once every thirty seconds under various circumstances when there is an abrupt change in RR interval between successive segments (see block 332 of FIG. 10, when there is a large jump in the segment average ST deviation (block 310 of FIG. 9), or when the ST deviation exponential average becomes close to a threshold (THP or THN in FIG. 13B or the thresholds in the table shown in FIG. 15).

In summary, the method comprises the steps of extracting ST segment information from beats within segments and generating a filtered ST time series therefrom. This filtered time series is labeled as "Current Filtered ST Deviation" in FIG. 3 and will also be referred to as "mStDevN_xavg" below. Current Filtered ST Deviation is then compared to a statistically generated, heart rate dependent ischemia detection threshold. If the Current Filtered ST Deviation persistently exceeds the threshold, then ischemia is detected.

Step 100 involves acquisition of a 10 second data segment, filtering, amplification, and analog-to-digital conversion by the IMD 3. The result is a digitized data segment comprising 2000 samples. In step 102, the high frequency noise content of the segment is assessed. In addition, if a segment has too many samples that saturate the voltage bandwidth, step 102 classifies the segment as noisy. Beat detection in block 104 is performed only on segments that step 102 has not rejected as too noisy. The RR interval between successive beats in the segment is determined in block 116, and beats associated with an abnormally short RR interval (e.g. premature ventricular contractions) are excluded from ST deviation calculations.

The next step 108 involves examining the QRS morphology of remaining beats by applying tests to various QRS parameters, for example the time between the maximum positive and maximum negative slopes. In block 110, the ST deviation for each normal beat is then computed according to the voltage difference between automatically determined ST and PQ points.

In block 112, the raw ST deviation for each beat is corrected for QRS amplitude based on a non-linear function of the average QRS amplitude of sinus beats in the segment. The correction is based, in part, on the statistical distribution of ST deviation as a function of QRS amplitude over a preceding time period. This feedback of ST deviation statistics is indicated by the dashed line from block 124 (discussed below) to block 112.

In block 114, the raw ST deviations are analyzed to determine whether the segment was contaminated by noise (such as motion artifact) within a frequency band high enough to disperse ST deviation measurements within a single segment (but low enough to avoid detection by the high frequency noise detection performed in block 102). Block 114 also involves additional noise analysis, as will be described below.

Step 122 involves the computation of the average QRS amplitude corrected ST deviation of acceptable beats within the current segment. Unless the segment meets certain exclusion criteria, this segment average updates an exponential average of ST deviation to generate Current Filtered ST Deviation. In step 120, the Current Filtered ST Deviation is added, again subject to certain exclusion criteria, to one of a set of ST deviation histograms where each member of the set corresponds to a range of RR intervals. ST(RR0) corresponds to the ST/RR histogram associated with the RR interval range RR0. More generally, ST(RRx) corresponds to the ST/RR histogram associated with the RR interval range RRx. The particular ST/RR histogram (ST(RRx)) that is updated depends on the RR interval which encompasses the exponential average of RR interval determined in block 118. QRS amplitude histograms will analogously be referenced as ST(QRx), where QRx is a range of QRS amplitudes.

In block 126, the Current Filtered ST Deviation is compared to an RR dependent ischemia detection threshold periodically determined by block 124. If the Current Filtered ST Deviation is persistently above or below upper or lower ST deviation thresholds, respectively, acute ischemia is detected.

Block 124 also periodically performs an analysis of the relationship between QRS amplitude (QR) and ST deviation. This analysis is based on data in a set of ST deviation histograms, where each member in the set corresponds to a range of QRS amplitudes, updated in block 120. The result of this analysis is QR dependent correction factors that parameterize QR correction performed in block 112.

Figure 4A:
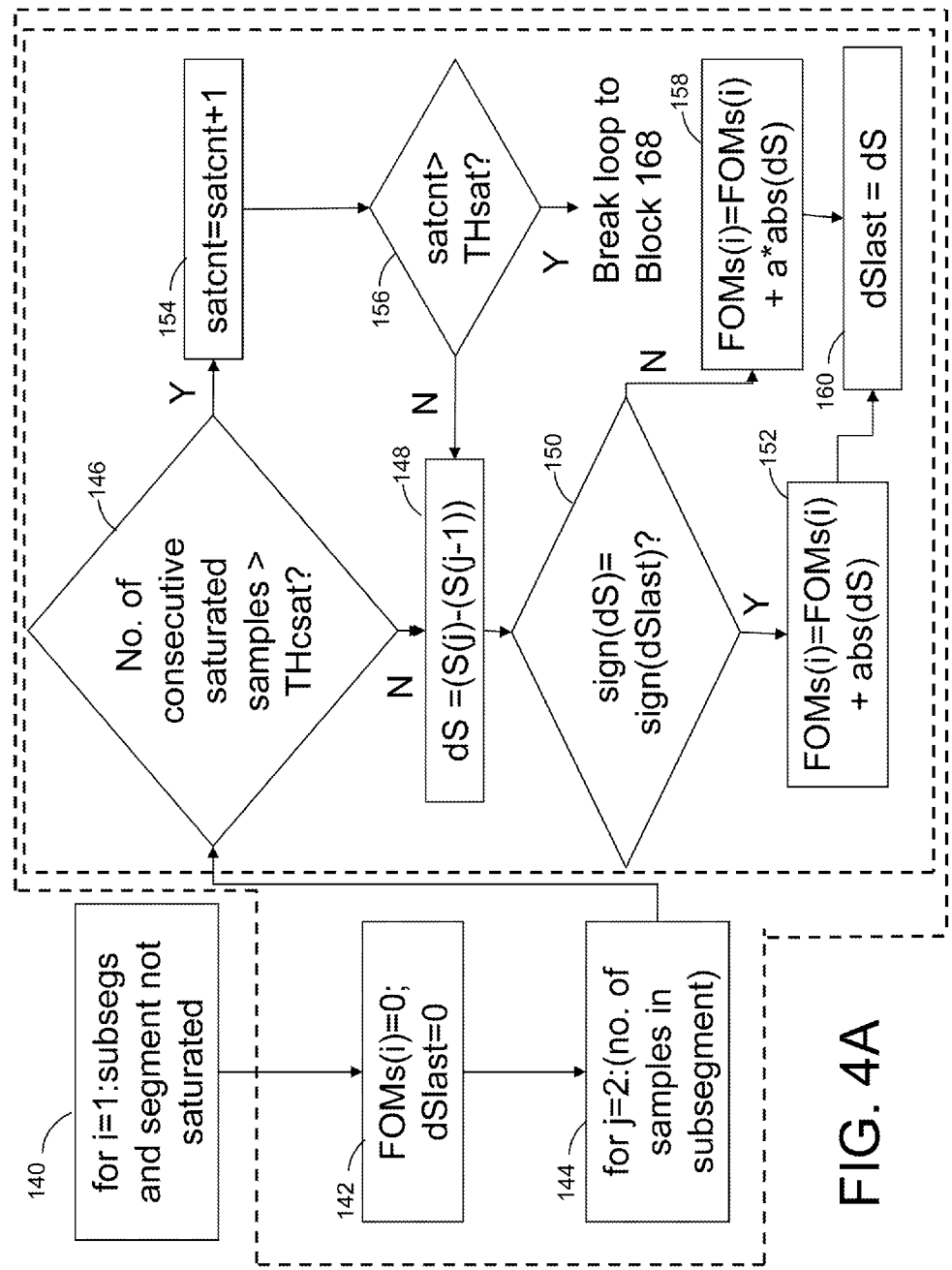
FIGS. 4A and 4B are a flow chart of a method for classification of a data segment according to its high frequency noise content and signal level.
Figure 4B:
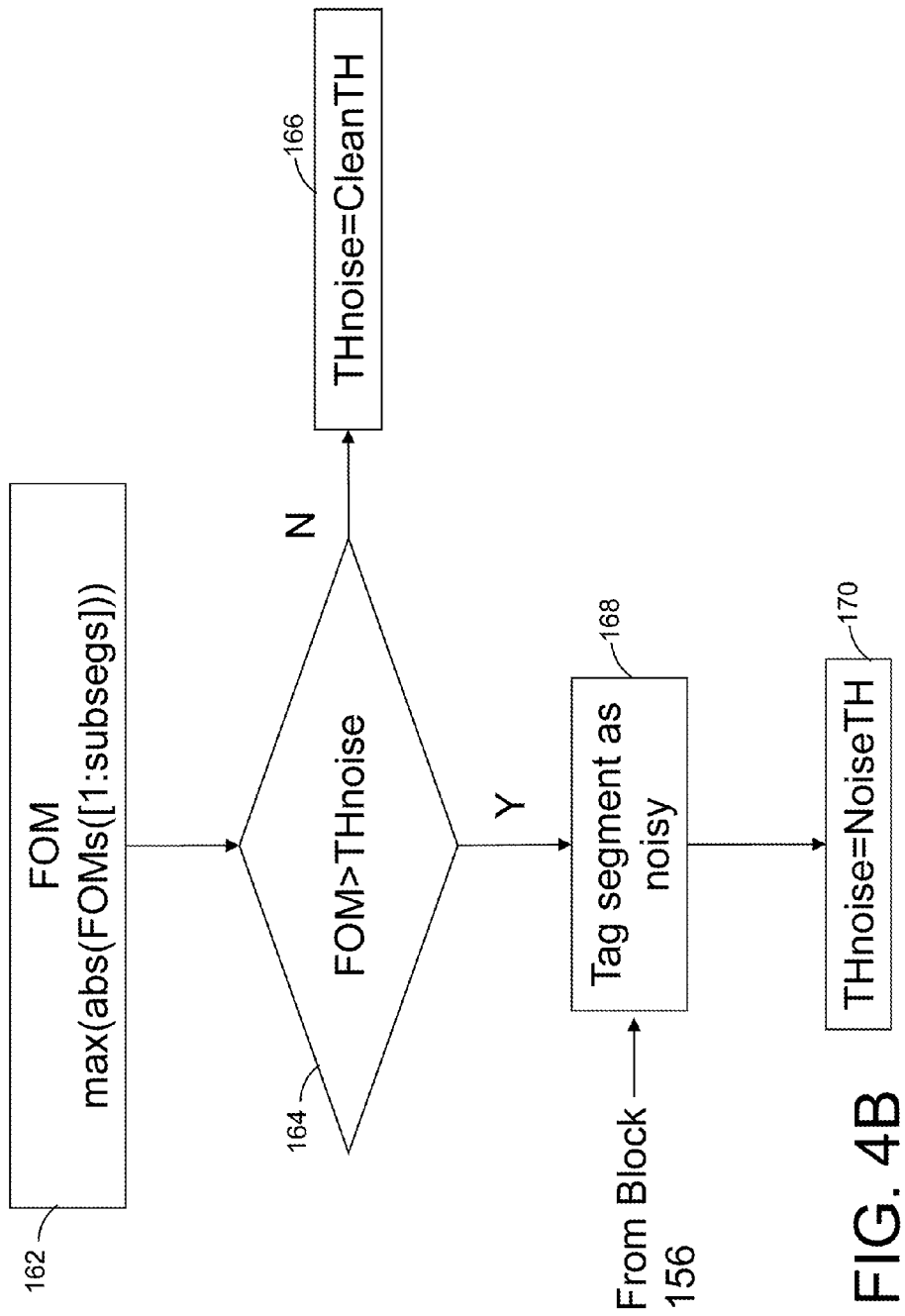

FIGS. 4A and 4B are a flow chart of step 102 (FIG. 3) for classification of a data segment according to its high frequency noise content and signal level. Block 140 is the initiation of a loop. In this Figure and in other Figures in this Specification, loops are shown as an initial block with the steps in the loop shown in a dashed line. In FIG. 4A, the steps within the loop are steps 142 to 160. In step 140, the loop is set to repeat so that a number of non-overlapping subsegments are separately assessed for noise. In the preferred embodiment, where a 10 second long segment consists of 2000 samples, the segment is divided into 3 subsegments. According to block 140, the loop is repeated for each of the subsegments or until a signal level saturation threshold is reached (block 156), whichever occurs first.

In block 142, a noise figure of merit (FOMs) variable for subsegment i is initialized to 0. A variable dSlast, which tracks the sign of signal changes, is initialized to 0. In block 144, a loop through each sample in subsegment i is initialized. In block 146, the number of consecutive saturated samples, which may be counted by a simple counter, is compared to a threshold THcsat, which is set to 6. If the number of consecutive saturated samples exceeds THcsat, control is transferred to block 154, in which a saturation counter (satcnt) is incremented. Block 154 then transfers control to block 156, which checks whether satcnt is greater than a threshold THsat, set to 100. If so, the segment is classified as noisy in block 168 (FIG. 4B). Otherwise, control transfers from block 156 to 148, where processing also continues if the condition in block 146 is not satisfied.

In block 148, the first difference of the signal S at the current sample (j) is computed. In block 150, the sign of dS (positive or negative) is compared to dSlast. If the signs are the same, control transfers to block 152, which increases FOMs(i) by the absolute value of dS. If the signs of dS and dSlast are different, control transfers to block 158, which increments FOMs(i) by a multiple (a) of dS. In this manner, changes in signal polarity increase the assessed noise level of the signal more than deflections of the signal in the same direction. Weighting FOMs(i) according to signal amplitude (dS) allows a segment to be considered not noisy if it contains high frequency, low amplitude signal fluctuations. In an alternative embodiment, FOMs(i) is weighted by dS normalized to a measure of the maximum voltage difference within the segment (i.e., max(S(k))−min(S(k)) over all k within the segment).

From either block 152 or block 158, control transfers to block 160, which sets dSlast to dS.

Once all subsegments have been processed (if the loops have not been broken based on the outcome of block 156), control transfers to block 162 in FIG. 4B. Block 162 sets the FOM for the segment as the maximum of the FOMs of the subsegments. In this and other Figures in this Specification, Matlab vector notation will be used to represent arrays such as FOMs=[FOMs(1) FOMs(2) FOMs(3)]=FOMs([1:3]).

Next, block 164 checks whether the segment FOM exceeds a threshold, THnoise. If not, in block 166, THnoise is set equal to a constant CleanTH. If the FOM of the segment exceeds THnoise, the segment is tagged as noisy in block 168, and THnoise is set equal to a threshold, NoiseTH, that is lower than CleanTH. In this manner, the noise threshold is characterized by hysteresis, whereby a segment is more likely to be classified as noisy if it follows a noisy segment.

Figure 5:
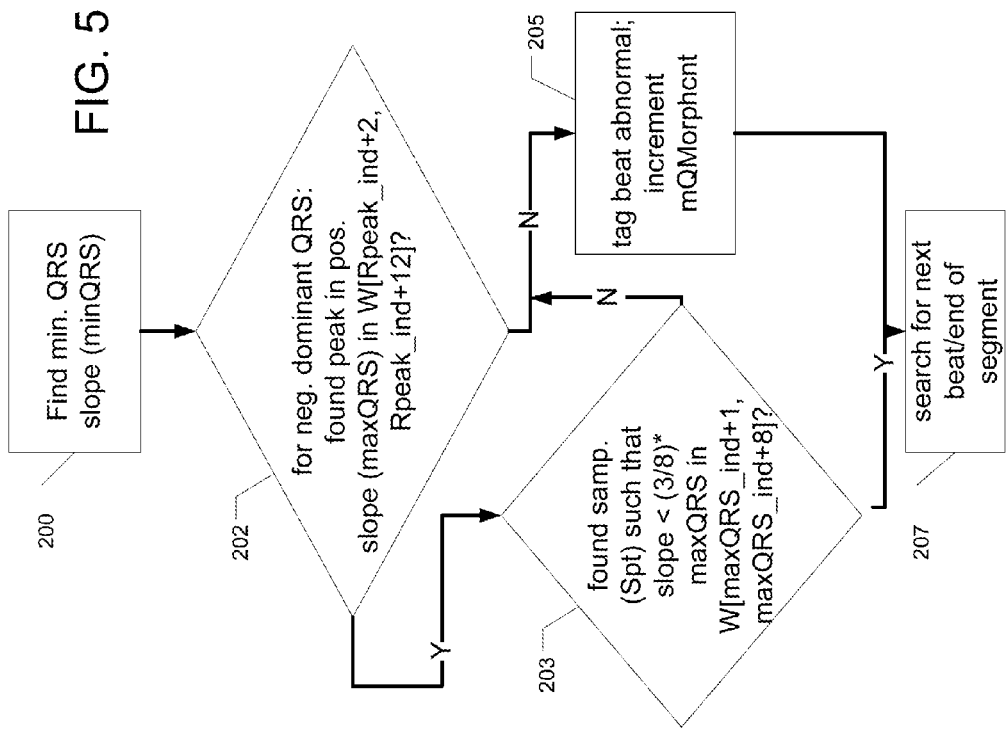
FIG. 5 is a flow chart of a routine that processes electrocardiogram/electrocardiogram segments to perform morphology checking on QRS complexes.

FIG. 5 is a flow chart of a routine that performs morphology checking on QRS complexes. QRS complexes are classified as normal or abnormal. ST deviation is not computed for abnormal beats. Blocks 200 through 207 are performed iteratively for each beat in a segment of electrocardiogram data. The steps shown in FIG. 5 are performed after QRS complexes have been detected in block 104 (FIG. 3), preferably by a routine based on the slope based scheme described in U.S. patent application Ser. No. 12/232,281, entitled "Methods and Apparatus for Detecting Cardiac Events Based on Heart Rate Sensitive Parameters", filed September 2008, owned by the assignee of the present invention. For each beat, the absolute minimum of the QRS (Rpeak) is located and the location of the preceding positive peak (initpk), if any, is determined. The average RR interval for the segment is computed. Based on the average RR interval, PVC beats are located, tagged, and not included in the segment's ST deviation. ST deviation is not determined for PVC beats.

For each non-PVC beat in the segment, the minimum QRS slope (minQRS) is located. For those beats that have a dominant negative QRS complex, block 202 searches for a positive peak in the slope (maxQRS) within a search window located after Rpeak. In particular, the search window begins at 2 samples after Rpeak and ends 12 samples after Rpeak. In the figures, a search window is denoted by W[a,b], where a is the window starting point (sample index integer) and b is the window ending point. The sample index (location) associated with a particular reference point is denoted by appending "_ind" to the particular reference point. For example, the index associated with Rpeak is Rpeak_ind.

If a local peak in the positive slope is found at either end of the purposely too wide search window designated in block 202, block 205 tags the beat as abnormal and increments the "bad beat counter" labeled as mQMorphcnt and in block 207 the routine searches for the next beat or the end of the segment. Otherwise, if block 202 has found a local positive slope peak, control transfers to block 203, which checks whether there is an appropriate decrease in the positive slope after maxQRS. In particular, within W[maxQRS_ind+1, maxQRS_ind+8], the routine searches for the first point where the slope is less than ⅜ of maxQRS. If no such sample can be found, the beat is tagged as irregular, and mQRMorphcnt is incremented in block 205, and processing continues in block 207. Otherwise, control passes from block 203 directly to block 207, which repeats the above process for each QRS detected in the segment.

Figure 6A:
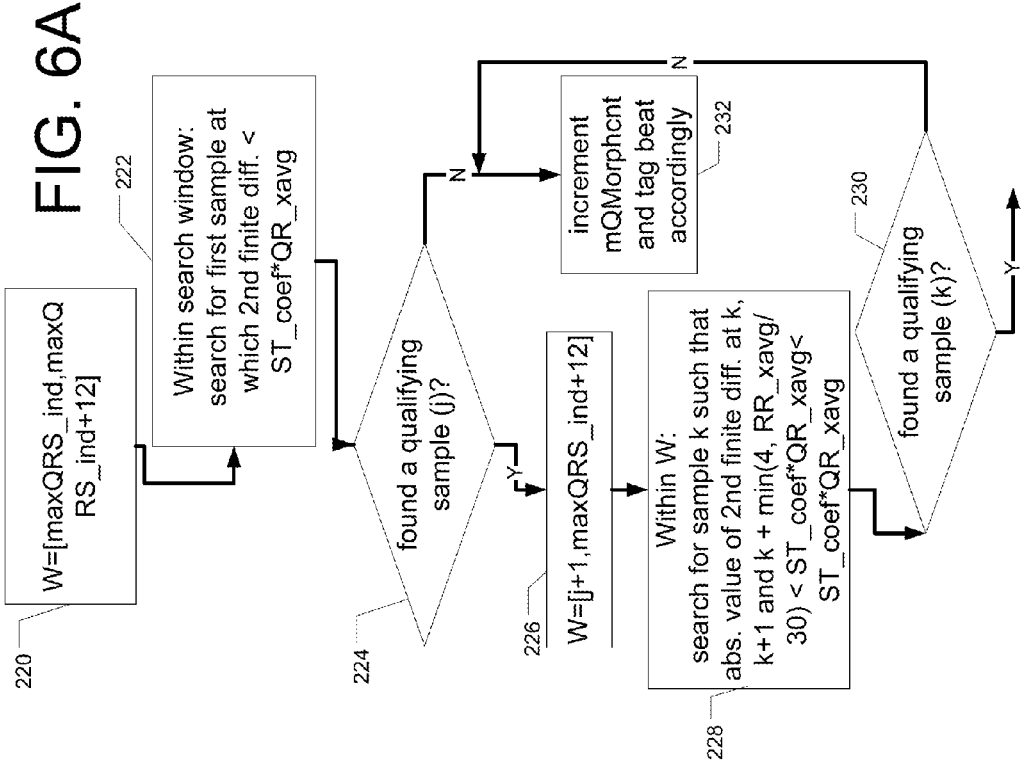

FIGS. 6A and 6B are collectively a flowchart that shows the preferred method for computing ST points. An analogous method may also be implemented to locate PQ points. In block 220 of FIG. 6A, the ST search window is set between maxQRS_ind+2 samples and maxQRS_ind+12 samples. In block 222, the slope of the slope ("second finite difference") of the signal is computed by twice applying the slope operator: $X(i+3)+2*X(i+2)+X(i+1)-X(i-1)-2*X(i-2)-X(i-3)$, where X(i) is the value of the waveform S at sample i for the first slope operation and then is the value of the slope at sample i for the second operation. The search stops at the first sample at which the second finite difference is less than a specified multiple (ST_coef) of QR_xavg, an exponential average of peak to peak QRS amplitude (QR). In the preferred embodiment, ST_coef is 1.

If such a qualifying sample is found (at sample j), block 224 transfers control to block 226, which sets a new search window starting at the sample after j (sample j+1) and again ending at maxQRS_ind+12. In block 228, this window is searched for two consecutive samples at which the absolute value of the second finite difference is less than ST_coef*QR_xavg.

If two such consecutive samples are found, with the latter of the two labeled as "k", control is transferred from block 230 to block 234 (FIG. 6B), which sets the ST point (ST_ind) based on the value of k, subject to constraints on the location of the ST point. In particular, the ST point must be at least 2 samples after the Spt (defined in block 203 of FIG. 5), and within a 3 sample window centered on Rpeak_ind+ST_int, where ST_int is an adaptive parameter that governs the location of the ST point.

Specifically, if k is within this three sample window, then the ST point (ST_ind) is chosen as the sample k. Otherwise, if k is before this window (i.e. closer to Spt than the beginning of this window), then ST_ind is set at the earliest sample in this window, Rpeak_ind+STint−1, subject to the previously mentioned constraint regarding the location of ST_ind relative to the Spt. If k is after the window, then then ST_ind is set at the latest sample in this window, Rpeak_ind+STint+1.

Block 234 then transfers control to block 236, which updates the adaptive parameter ST_int according to the number of samples between ST_ind and Rpeak. ST_int is preferably updated according to an exponential average filter. The exponential average of a variable (V) is expavg(V, Δ, α, min, max, mindelt, maxdelt), which means that the variable V is updated by the current value Δ, with an update weighting $\frac{1}{2}^\alpha$, subject to constraints on the maximum and minimum allowable value for the variable and changes in that variable. Ignoring the constraints, expavg(V, Δ, α, ( ), ( ), ( ), ( )) is $V(j+1) = (2^\alpha-1)*V(j)+\Delta)/2^\alpha$.

Returning to block 224, if no second finite difference within the ST point search window was less than the threshold, then control transfers to block 232, which increments mQMorphcnt. Similarly, if no qualifying sample is found in block 230, control is transferred to block 232.

The routine shown in FIGS. 6A and 6B may be modified to locate PQ points. In this case, the preferred search window (block 220) is (MinQRSInd−4, MinQRSInd−20). ST_coef in block 1004 is −1 while the absolute value of ST_coef, 1, is used in block 222. The sign of ST_coef will depend on expected QRS morphology; in the case of a QRS with a V2 like morphology (small R, large S), the curvature of the PQ and ST segments have opposing signs. In block 234, the PQ point is not allowed to come within four samples of the R wave peak (i.e., maximum value of the initial upstroke of the QRS before the large downstroke.)

FIG. 7 is a flowchart that shows steps for determining a measure of segment based ST deviation (mStDevN_xavg), which is an averaged, effectively filtered version of a number of beat based ST deviation measurements. Steps 250 through 260 are performed for each (provisionally) analyzable beat that has associated ST and PQ points. In block 250, ST deviation (Stdev) is determined by the difference between the signal values of the samples surrounding the ST and PQ points, respectively. In the preferred embodiment, the PQ signal value is equal to the average of the signal over four consecutive samples starting at the sample that is two samples earlier than the PQ point. In the preferred embodiment, the ST signal value is equal to the average of the signal over four consecutive samples starting at the sample that is one sample earlier than the ST point.

Figure 11:
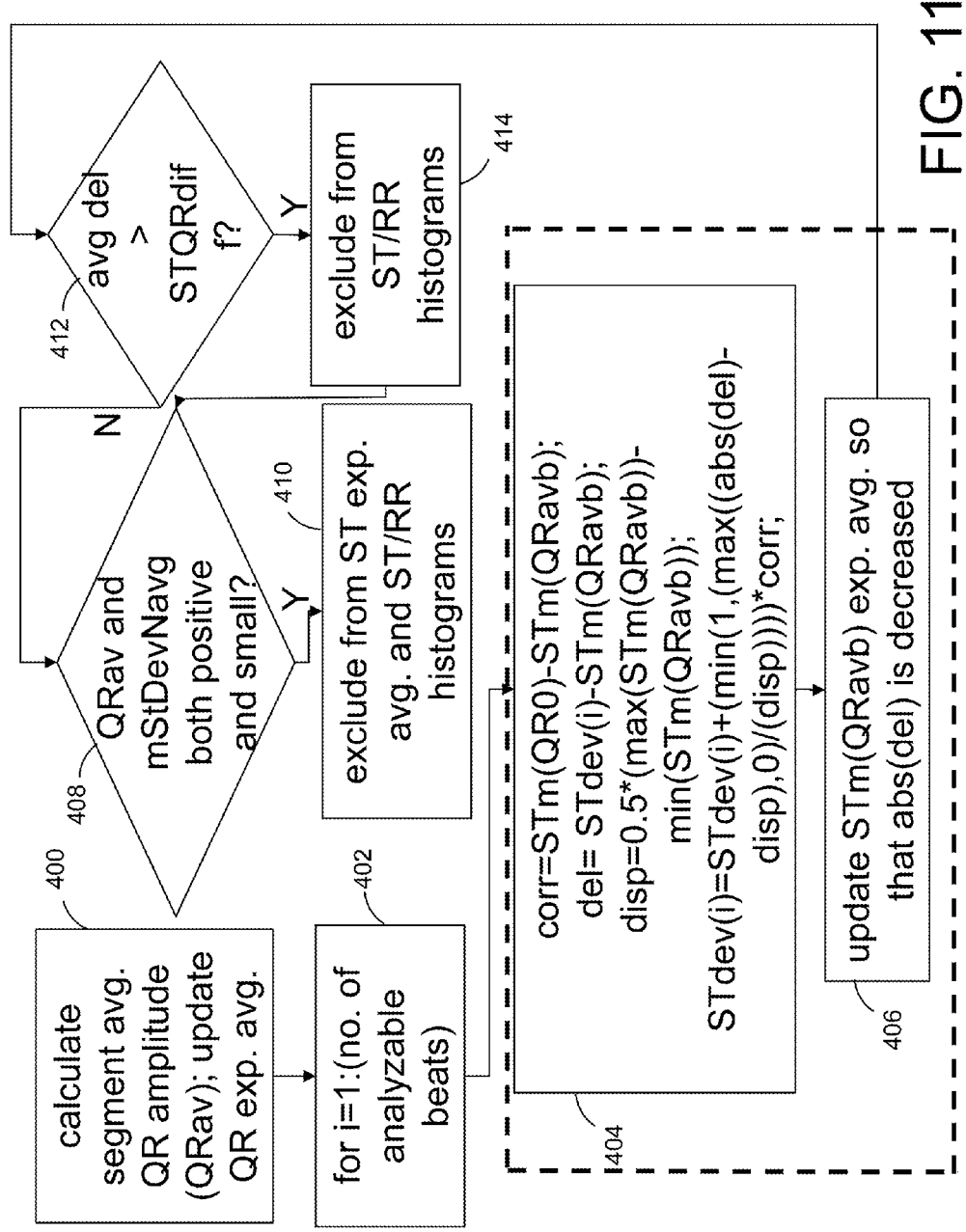
FIG. 11 is a flowchart that shows steps for correcting ST deviation according to QRS amplitude.

Stdev is corrected for QRS amplitude in block 254 according to the method described in FIG. 11. Control passes to block 256, which checks whether the difference between both (i) Stdev and the median ST deviation at the resting heart rate (STm(RR0)); and (ii) Stdev and the current long term ST deviation exponential average (mStDevN)_xavg), exceed a threshold maxchg. If so, the beat is tagged as non-analyzable in block 260 and does not figure into the segments average ST deviation. Otherwise, an analyzable ST deviation beat counter is incremented in block 258. The segment average ST deviation (mStDevNavg) is calculated in block 262.

Processing continues at block 300, shown in FIG. 8, which is a flow chart of a routine that analyzes a segment's ST deviation values and other segment characteristics to determine whether the segment's average ST deviation (mStDevNavg) should contribute to long term current filtered ST deviation (see block 122 of FIG. 3), ischemia diction, and ST/RR histograms. Block 300 performs a number of tests to determine whether the current segment's ST deviation (mStDevNavg) should be considered valid for two purposes: (1) ischemia detection; and (2) contributing to the ST/RR histograms. If a segment is too abnormal, or appears to correspond to a rapid change in physiological state (e.g. a change in heart rate), as defined by the tests in block 300 (and block 306 described below), its ST deviation can not be relied on for ischemia detection or for contributing to ST/RR statistics. The three tests are: (1) whether the average RR interval of the current segment is within ¾ and 1.5 times the average RR interval of the previous segment; (2) whether mQMorphCnt (see blocks 205 of FIG. 5 and block 232 of FIG. 6A) is low; and (3) whether the number of PVC's is low (less than 2). If either test 1 or tests 2 and 3 are positive, then the segment's ST deviation may qualify for ischemia detection/statistics, so block 302 transfers control to block 304. Otherwise, if both test 1 and tests 2 or 3 are negative, block 302 transfers control to block 332 of FIG. 10, which results in the exclusion of the segment's ST deviation from ischemia detection/statistics (by skipping past block 316 of FIG. 9).

Returning to the "yes" branch of block 302, block 304 calculates a measure of the noisiness (STFOM) of the ST deviations of the beats in the current segment. If the segment was contaminated by noise such as motion artifact, the variance of the ST deviations will tend to be relatively large, which in turn implies that the average ST deviation should not be trusted. To assess ST deviation noise/variance, the routine described with reference to FIG. 4A is applied with the ST deviation of each individual (analyzable) beat constituting signal S, and with the signal saturation steps (146, 154 and 156) excluded. After the ST deviations of all the analyzable beats have been processed, the resulting FOM (block 152 of FIG. 4A) is normalized by the number of analyzable beats in the current segment, and the result is the STFOM.

In block 306, STFOM is compared to a threshold. If the threshold is exceeded, control passes to block 332 of FIG. 10, which results in the exclusion of the segment's ST deviation from ischemia detection/statistics. Otherwise, processing continues in block 310 of FIG. 9. (In an alternative embodiment, STFOM controls the weighting of the ST deviation exponential average updating, with an inverse relationship between the magnitude of STFOM and the amount the current segment's ST deviation contributes to the long term exponential average in block 314 of FIG. 9.)

Block 310 (FIG. 9) checks whether the difference between mStDevNavg and the current long term, filtered ST time series (mStDevN_xavg) exceeds a threshold. If so, mQMorphcnt is incremented in block 312 and the segment is not added to the ST/RR histograms. Subject to block 410 of FIG. 11, which describes an additional criterion for excluding mStDevNavg from contributing to mStDevN_xavg, control then passes to block 314, which is also invoked from the "no" branch of block 310. In block 314, the Filtered exponential average (mStDevNavg) is updated according to mStDevNavg. In block 316, if the result of the block 310 test was negative, mStDevN_xavg is added to the ST/RR histograms. Details regarding ST/RR histograms are described in U.S. Pat. No. 7,512,438, entitled "Implantable System for Monitoring the Condition of the Heart", owned by the assignee hereof. The exponential average of the RR interval time series determines which of the ST(RRx) histograms is incremented.

In an alternative embodiment, block 310 applies additional tests to help prevent noisy data from being added to ST/RR histograms. One additional test is to compare the current mStDevNavg with the most recent prior mStDevNavg. If the difference between the two exceeds a threshold, the histograms are not updated. In yet another alternative embodiment, a measure of the dispersion of the past few mStDevNavg results is computed and compared to a threshold. If the dispersion is too large, histograms are not updated. Measures of dispersion include, without limitation, standard deviation and a sum of first order differences (absolute values) from the mean.

Figure 9:
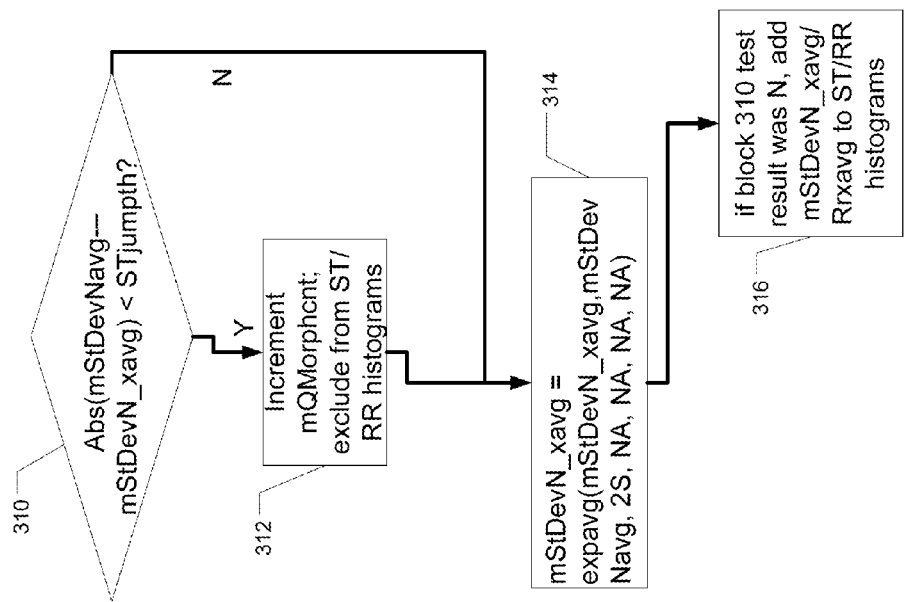
FIG. 9 is a routine that computes long term Filtered measure of ST deviation according to an exponential average filter.
Figure 10:
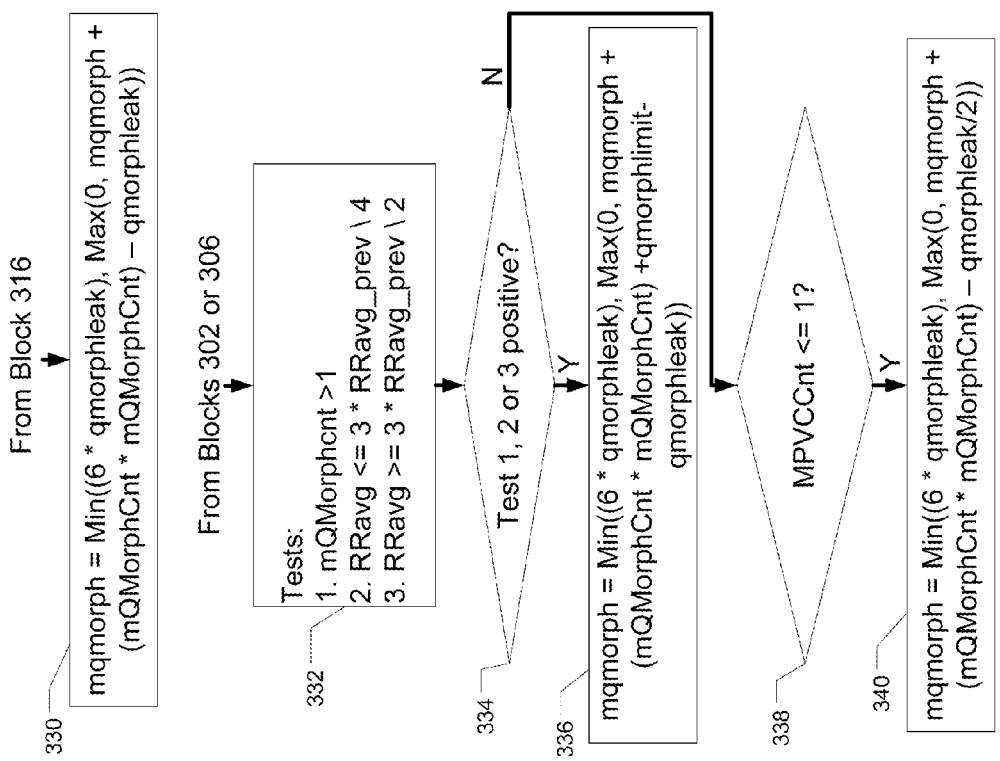
FIG. 10 is a routine that maintains a counter that tracks the relative frequency of abnormal beats based on characteristics other than ST deviation.

FIG. 10 is a flow chart of a routine that tracks the relative frequency of variant beats. Variant beats are broadly defined as beats that deviate from an established pattern of normal sinus rhythm beats. Variant beats include beats that resulted in an increment of mQMorphcnt during the QRS processing described with respect to FIG. 5. In addition, mQMorphcnt is also updated in block 232 (FIG. 6A) and block 312 (FIG. 9). The relative frequency of variant beats is stored in a variable mqmorph. If mqmorph is above a threshold for a certain period of time, the system is preferably configured to respond in a user-programmable manner such as generating an alarm.

The mqmorph variable is updated after each segment is processed. The manner in which mqmoprh is updated depends on the outcome of the tests applied in blocks 302 and 306 (FIG. 8). If the outcome of this test suggests that the current segment is relatively "normal", mqmorph is computed in block 330. In particular, in block 330, mqmorph is increased by $mQMorphCnt^2$—qmorphleak, subject to the constraints that mqmorph can not be negative or greater than 6*qmorphleak, where qmrophleak is a parameter. According to the above equation that updates mqmroph, qmorphleak acts like a "drain" that tends to "empty" mqmorph. Thus, mqmorph tends to remain at a low value unless there are a number of segments within a relatively short period of time with relatively high mQMorphCnts.

If the segment is considered relatively "abnormal" according to the tests applied in blocks 302 or 306, control passes to block 332. If mQMorphcnt is greater than 1 or the segment's average RR interval is very different from the previous segment's RR interval, then mqmorph is increased in block 336 by $mQMorphCnt^2$+qmorphlimit-qmorphleak, subject to the same constraints on the maximum and minimum mqmorph values described with respect to block 330.

Returning to block 332, if none of tests 1, 2 or 3 is positive, then control passes to block 338, which determines whether the number of PVC's is low (less than 2). If so, block 340 increases mqmorph in the same manner as block 330 except that qmorphleak is divided by 2.

FIG. 11 is a flowchart that shows steps for correcting ST deviation according to QRS amplitude (QR). In block 400, the segment average QR amplitude (QRav) is computed based on the values of all analyzable beats in the segment, i.e. those beats whose ST deviations are eligible to contribute to segment average ST deviation (mStDevNavg). Also, an exponential average of QR amplitude is updated based on QRav as follows: QR exp. avg=expavg(QR exp. avg., QRav, 2, NA, NA, NA, NA).

Block 402 is the beginning of a loop over all of the analyzable beats. In block 404, the ST deviation (STdev(i)) of the analyzable beat i is corrected by adding a term min(1,(max ((abs(del)−disp),0)/(disp))))*corr, where corr=STm(QR0)−STm(QRavb), del=STdev(i)−STm(QRavb), disp=0.5*(max (STm(QRavb))−min(STm(QRavb)). STm(QR0) is the median ST deviation associated with the median QR amplitude. STm(QR0) is computed from ST/QR histograms, as will be further described with reference to FIG. 12. Similarly, STm(QRavb) is a quasi-median ST deviation for the QR bin associated with the QR amplitude of the current segment (QRav). (More specifically, QRavb in the expression is the QR bin corresponding to the QR range in which QRav falls.) STm(QRavb) is computed from ST/QR histograms, as will be further described with reference to FIG. 12, and is further modified in block 406, as will be discussed below.

The correction (corr) is not added directly to STdev(i). Instead, the amount of the correction (corr) that is added to STdev(i) depends on how close STdev(i) is to its expected value, which is STm(QRavb). If STdev(i) varies substantially from this expected value, then there is less confidence that the correction corr is appropriate. The quantity disp controls the amount of corr that is added as a function of the difference (del) between STdev(i) and STm(QRavb).

In step 406, STm(QRavb) is updated to decrease del. For example, if the uncorrected STdev(i) was larger than STm (QRavb), then STm(QRavb) is slightly increased.

Returning to segment based processing, in block 412, the average del over the segment is compared to a threshold. If the average del exceeds the threshold, the segment ST deviation (mStDevNavg) is excluded from the ST/RR histograms in block 414. Block 408 tests whether both QRav and mStDevNavg are positive but sufficiently small that the applicable ST/QR histogram has few if any entries. If so, then block 410 excludes mStDevNavg from both the ST/RR histograms and the update of the ST exponential average (block 314 of FIG. 9). Exclusion is appropriate because small positive values of both QRav and mStDevNavg could result from a device related factor such as high lead impedance. To enable the system to adapt to new, low values of QRav and mStDevNavg, mStDevNavg (not mStDevN_xavg) is added to the appropriate ST/QR histogram.

Figure 12:
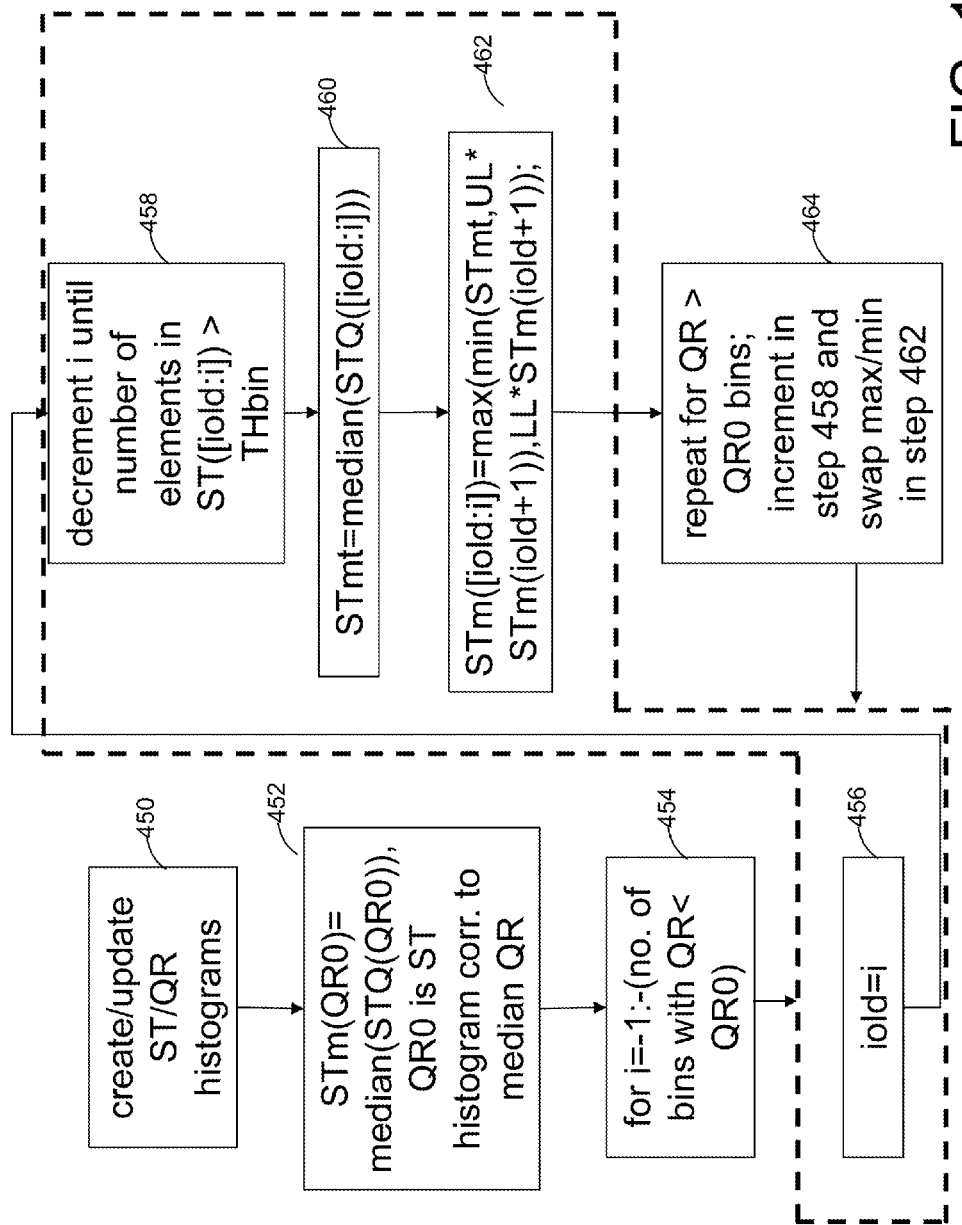
FIG. 12 is a flowchart of a routine that calculates parameters for QRS amplitude correction.

FIG. 12 is a flowchart of a routine that calculates parameters for QRS amplitude correction required by the routine described with reference to FIG. 11. In block 450, an array of ST deviation histograms are created and/or updated, which each histogram corresponding to a range of QRS amplitudes (QR), measured as the difference between the maximum and minimum waveform values of the QRS complex. Techniques for creating arrays of ST deviation histograms are described in U.S. Pat. No. 7,512,438, entitled "Implantable System for Monitoring the Condition of the Heart", owned by the assignee hereof. The ST/QR histograms are updated with the QR exponential average (block 400, FIG. 11) after every segment for which the QR exponential average was updated.

In block 452, the median ST deviation (STm(QR0)) for the median QR histogram is computed. STm refers to median ST deviation, while the x in STm(QRx) refers to the QR histogram x. QR0 refers to the median QR histogram. For example, if there are ten ST deviation histograms as a function of QR amplitude, one histogram each for the QR ranges 1-10, 11-20 . . . , 91-100, and the median QR amplitude is 77, then QR0 refers to the ST deviation histogram associated with the QR range 71-80. In this example, the histogram associated with the range 61-70 would be QR-1, the histogram associated with the range 81-90 would be QR1, the histogram associated with the QR range 51-60 would be QR-2 etc.

Block 454 is the beginning of a loop that first processes each ST(QRx) histogram associated with QR<QRm and then processes each ST(QRx) histogram associated with QR>QR0. The current histogram being processed is tracked by index i. In block 456, the current index i is stored. In block 458, i is decremented until the number of elements in consecutive histograms exceeds a threshold, THbin. For example, if i=−1, THbin is 200, and the number of elements in STQ(QR-1) is 240, then i is not decremented at all. As used above, "number of elements" refers to the sum over all bins within a particular histogram. Returning to the above example, if the number of elements in STQ(QR-1) is 150 and the number of elements in STQ(QR-2) is 70, then i decremented once. The number operator n will refer to the number of elements in a histogram or array of histograms. Continuing with the above example, N(STQ([−1:−2]))=220.

In block 460, the median ST deviation over the current set of ST(QRx) histograms ST([iold:i] is calculated. In block 462, the quasi-median ST (STQm([iold:i])) for the current set of ST(QRx) histograms is set as max(min(STQm,UL*STm(iold+1)),LL*STm(iold+1)), where UL and LL are parameters that control the amount by which the current quasi-median is allowed to vary from the median ST of the adjacent QR histogram (STm(iold+1). Preferred values of UL and LL are 1.2 and 0.5, respectively, so that the quasi-median is not allowed to exceed 1.2 times the adjacent quasi-median or be less than 0.5 times the adjacent quasi-median. (When proceeding in the direction of larger QR values (block 464), the max and min statements in block 462 are reversed.)

In block 464, the above described process beginning with block 456 is repeated for ST histograms associated with QR>QR0.

Figure 13A:
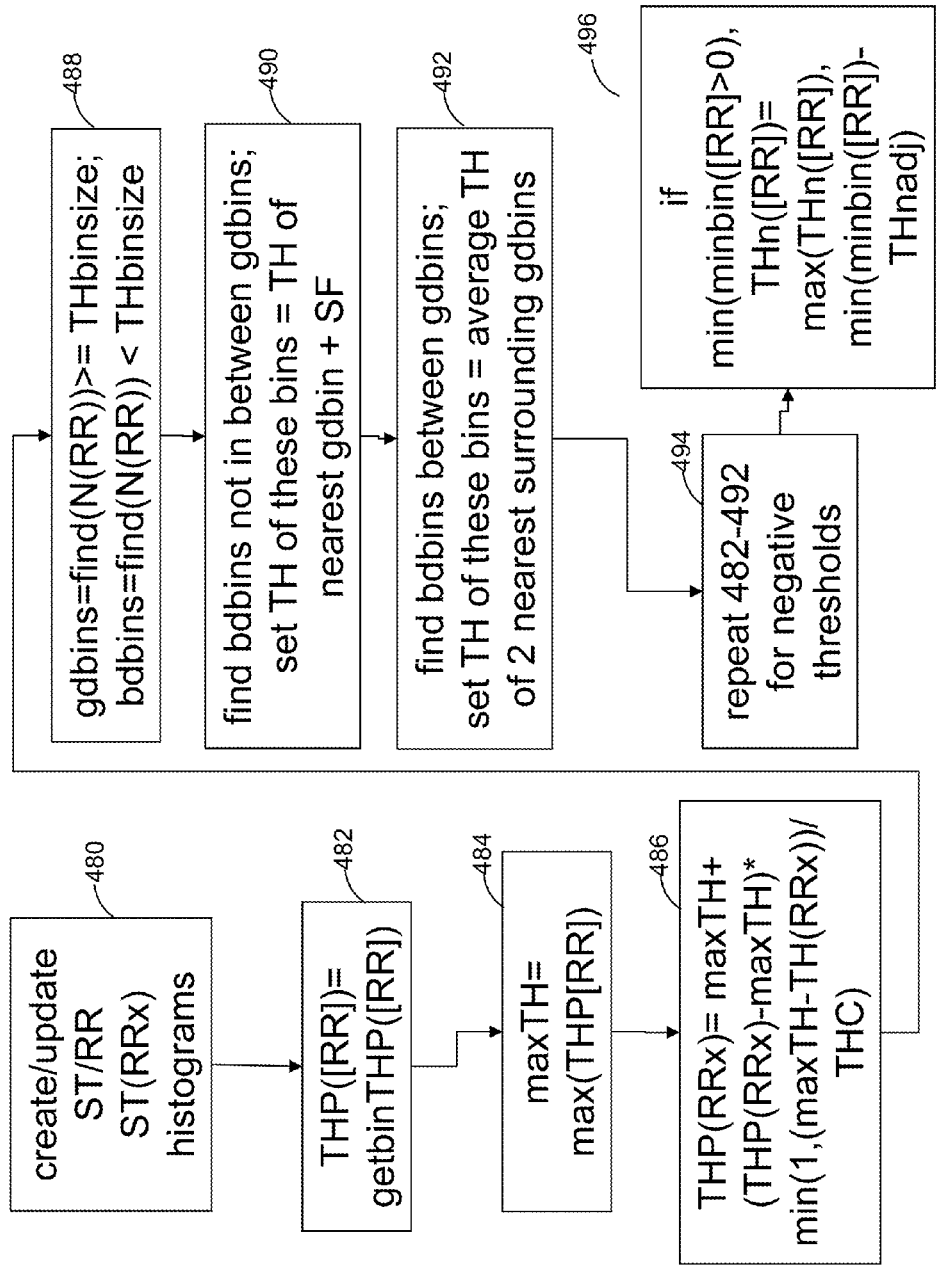
FIGS. 13A and 13B are a flowchart of a method for determining ST deviation ischemia detection intervals according to RR interval.
Figure 13B:
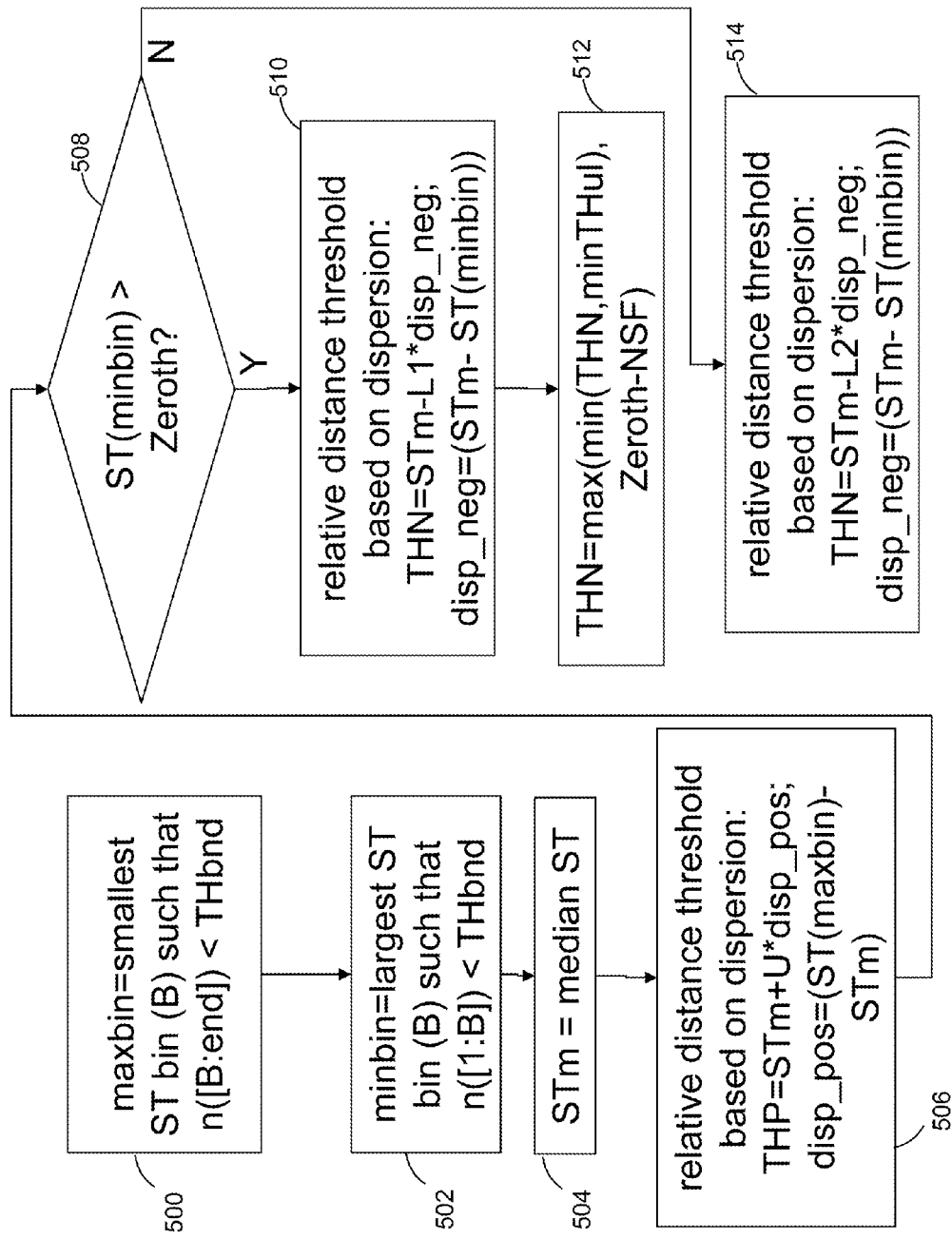
Figure 14A:
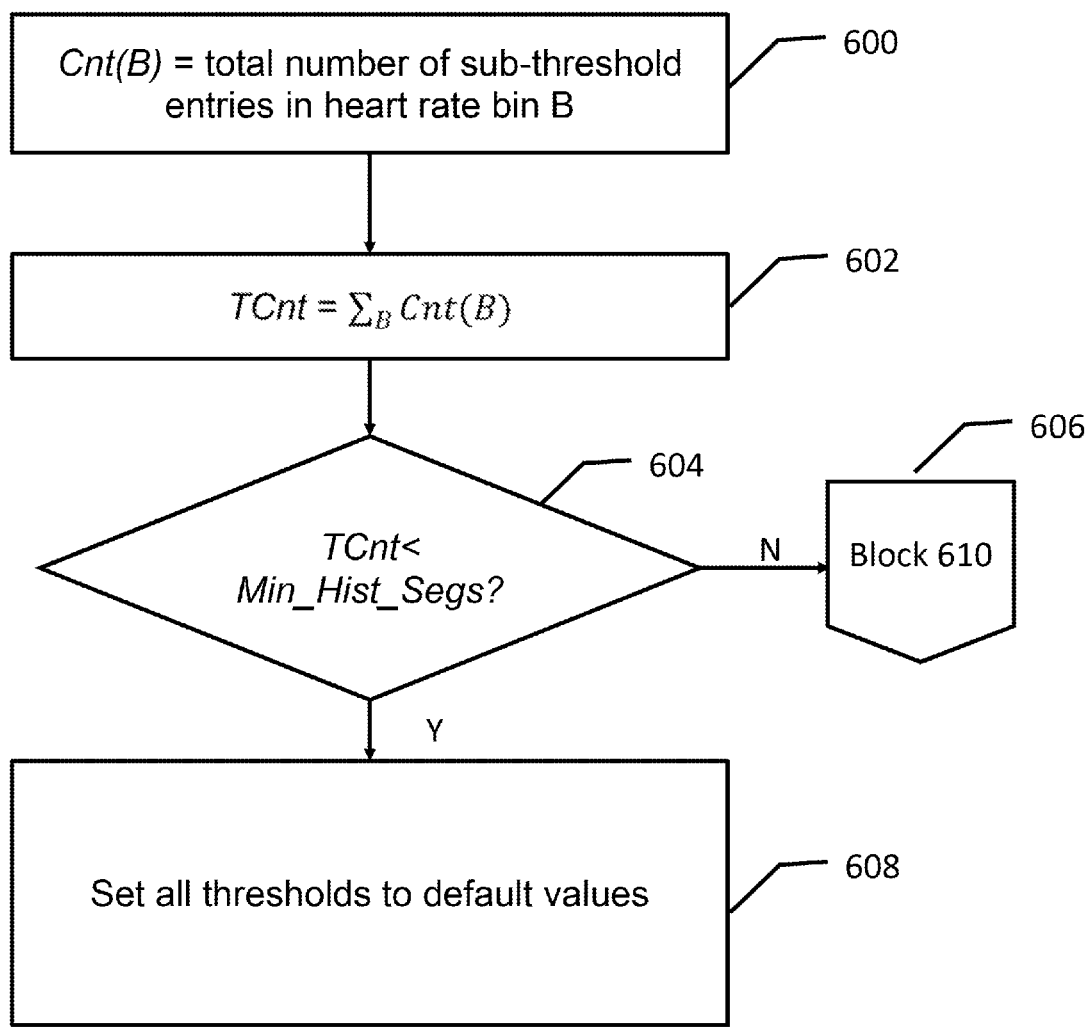
FIGS. 14A-14F are flowcharts of an alternative method for determining ST deviation ischemia detection intervals according to RR interval.
Figure 14B:
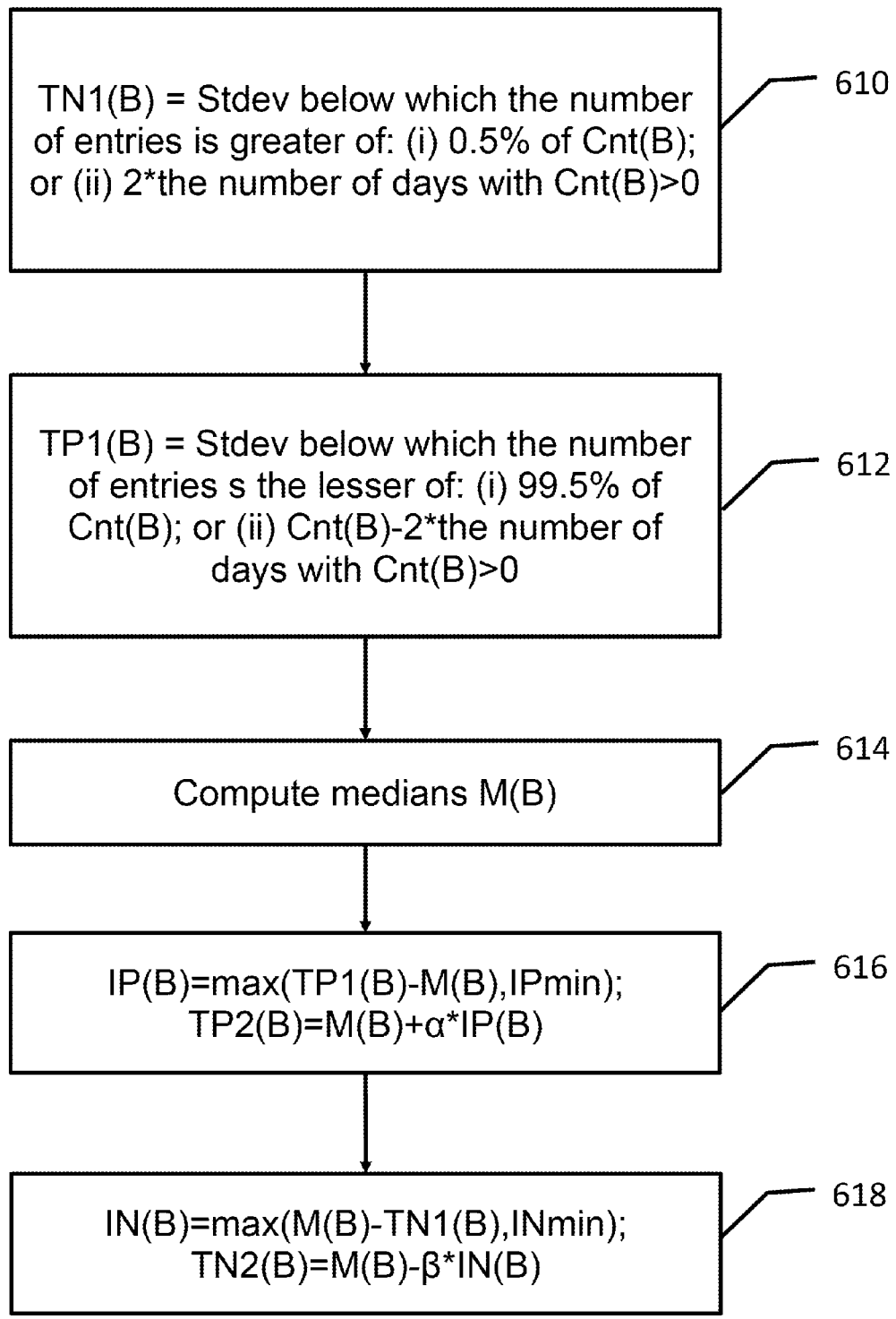
Figure 14C:
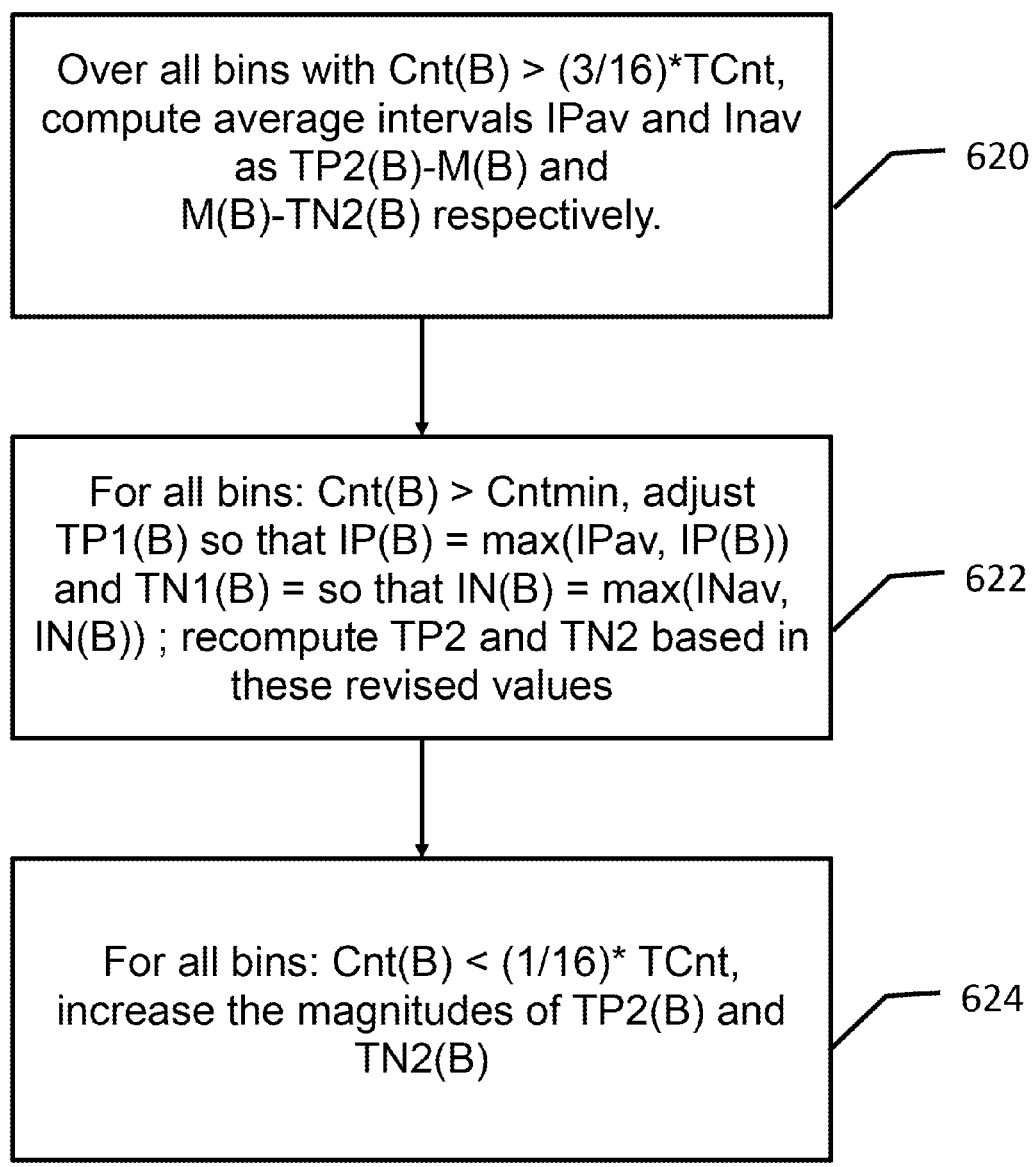
Figure 14D:
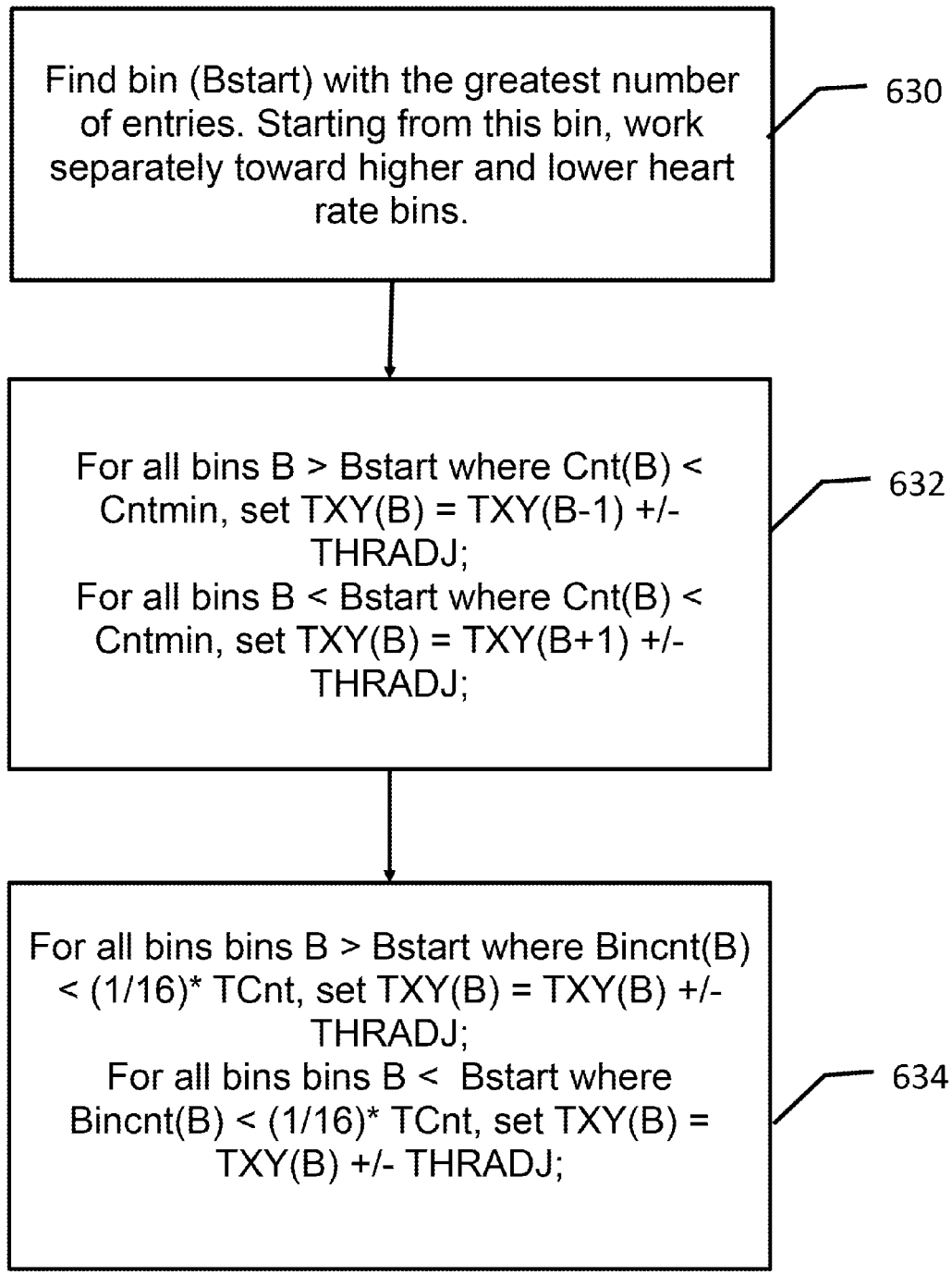
Figure 14E:
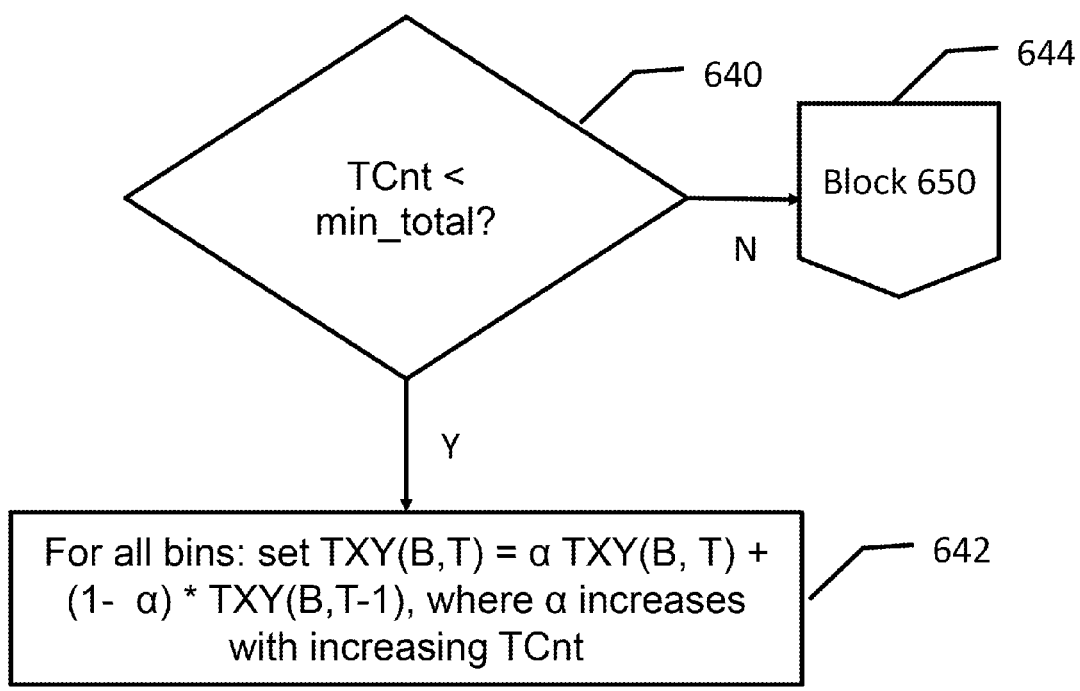
Figure 14F:
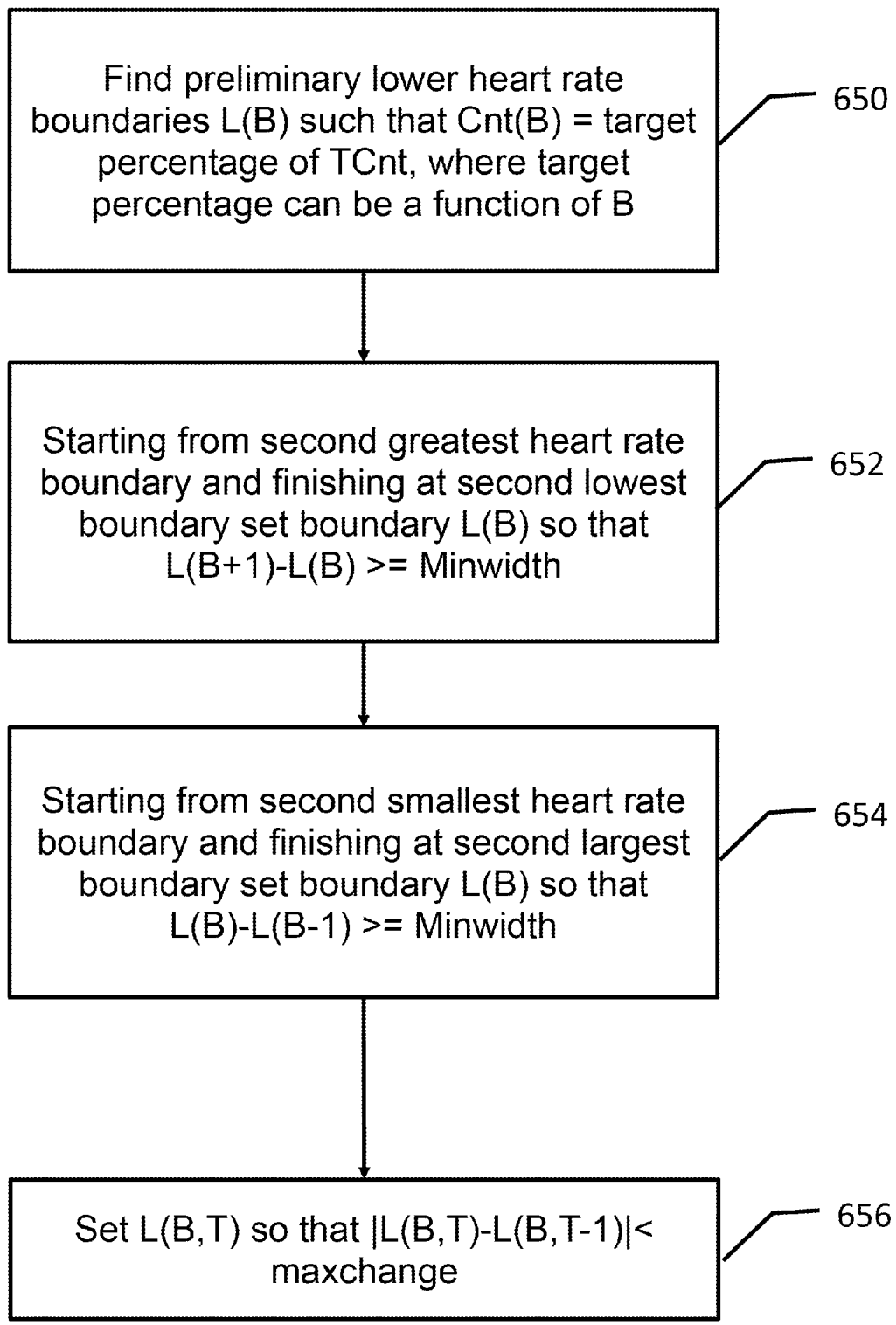

FIGS. 13A and 13B are a flowchart of a process for setting ST deviation thresholds for detecting acute ischemic events. In block 480, an array of ST deviation histograms are created and/or updated, which each histogram corresponding to a range of RR intervals. Techniques for creating arrays of ST deviation histograms are described in U.S. Pat. No. 7,512,438, entitled "Implantable System for Monitoring the Condition of the Heart", owned by the assignee hereof. An exponential average of the average segment RR interval preferably determines which ST(RRx) histogram is accessed. This histogram is updated with mStDevN_xavg, as previously described.

The threshold setting process will first be described for positive ST deviation thresholds, i.e. thresholds for detection of ST deviations that are greater than normal. An analogous procedure sets negative ST deviation thresholds, i.e. thresholds for detection of ST deviations that are less than normal.

In block 482, the positive ST deviation threshold for each RR interval is determined according to the process to be described with reference to FIG. 13B. For example, if there are 5 RR ranges, from 301 ms-500 ms, 501 ms-700 ms, 701 ms-800 ms, 701 ms-900 ms, and 900 ms-2000 ms, then there are 5 ST(RRx) histgorams. The notation [RR] means that the separate RR ranges are to be taken as a vector. Continuing with the above example, ST([RR])=ST([1:5]). The threshold function (implemented by the routine in FIG. 13B), is indicated by TH( ). Thus, in the above example, TH([RR]) is an array with 5 thresholds, one corresponding to each RR array, i.e. [TH(1) TH(2) TH(3) TH(4) TH(5)].

In block 484, the maximum threshold over the threshold array is determined. In block 486, the thresholds are set equal to maxTH+(TH(RRx)−maxTH).*min(1,(maxTH−TH(RRx))/THC), where THC is a constant that depends on the dynamic range of the ST measurements. If a typical ST range is between 0 and 1000, then a preferred value for THC is 2000. For example, TH(1) is equal to maxTH+(TH(1)−maxTH).*min(1,(maxTH−TH(1))/THC).

In block 488, the RR arrays with a sufficiently large number of entries, i.e. at least THbinsize elements, are located and identified as "gdbins." Again, the number operator N refers to the number of elements in a particular histogram. Similarly, the RR arrays with less than THbinsize are located and identified as bdbins. In block 490, for any bdbin that is not between gdbins, the threshold is set as the threshold of the nearest gdbin+SF, where SF is a safety factor. In block 492, for bdbins inbetween gdbins, the threshold is set as the average of the two nearest surrounding gdbins.

In block 494, steps 482-492 are repeated for negative thresholds. For this processing, the max operator in block 484 is replaced with the min operator, and (maxTH−TH(RRx))/THC in block 486 is replaced with −(minTH−TH(RRx))/THC.

In an alternate embodiment, instead of correcting ST deviation for QR (FIG. 12) and setting RR dependent thresholds (FIGS. 13A-13B), thresholds are set directly based on both QR and RR, which comprise a two dimensional parameter array. For example, if there are 8 QR ranges and 5 RR ranges, separate ST deviation statistics are kept for each of 40 bins. Thresholds are set as in FIG. 13A, with two dimensional interpolation/extrapolation in blocks 490 and 492 instead of one dimensional interpolation/extrapolation.

Finally, step 496 increases negative thresholds in the cases where the minimum negative ST deviation boundary (minbin) (described further below with respect to FIG. 13B) over all RR intervals is greater than 0. In this case, for reasons similar to those set forth below with regard to step 512 of FIG. 13B, the lower threshold (THn(RRx)) for each RRx interval is changed to a value based on the minimum lower threshold (min(THn(RRx)) plus an adjustment factor THnadj. For example, assuming that there are only two RRx ranges, and that the minimum ST deviation occurs in the second range (RR2), the minbin for RR2 is 50, and that the threshold for RR2 is −200, the negative threshold for RR2 is raised to −150 if THnadj is set to 100. Conversely, if the negative threshold for RR2 (before block 496 is invoked) is −125, then the threshold for RR2 remains at −125, since −125>−150. THn(RR1) is also increased to −150 if it was lower than that value. It will be appreciated that the choice of lead polarity is arbitrary, so that the above adjustments may apply to the positive thresholds depending on lead orientation and polarity.

FIG. 13B is a flowchart that shows the steps for computing the positive and negative detection thresholds for a particular ST(RRx) histogram. This routine is invoked by block 482 of FIG. 13A. In block 500, the upper ST deviation boundary bin (maxbin) is found by locating the bin for which the sum of all elements in the bin and in bins with larger ST deviations is less than a threshold THbnd. For example, if there are 10 ST bins that cover ST deviations in the ranges of 0-9, 10-19 . . . . 80-89 and >90, respectively, and there are 15 elements in bin 70-79, 5 elements in bin 80-89 and 3 elements in bin >90, and THbnd is 10, then maxbin is bin 80-89 since there are less than 10 elements collectively in bin 80-89 and above but more than ten elements collectively in bin 70-79 and above.

THbnd depends on the number of entries in a histogram. THbdn is preferably set at THbndbase*NH, where THbndbase is the desired ST deviation cutoff per unit time, and NH is amount of time during which data has been inserted into the histogram. For example, if THbndbase is 10 entries/day, and a histogram has 5 days of entries, then THbnd is 50.

In block 502, the lower ST deviation boundary bin (minbin) is found analogously to the procedure described with reference to block 500.

In block 504, the median ST (STm) is found for the histogram ST(RRx). In block 506, the positive threshold (THP) is set equal to STm+U*disppos, where disp_pos=(ST(maxbin)−STm) and U is a programmable parameter. (The RRx parenthetical is implied for quantities such as THP, STm and is not shown in blocks 506-514.) Continuing with the above example, where maxbin corresponds to ST deviations between 80-89, ST(maxbin) is set equal to 85, the midpoint (in terms of ST deviation) of maxbin. If the median ST over all bins is 50 and U is 2, then THP is 50+2*(85−50)=120. The threshold THP is thus a function of the dispersion rate of the ST(RRx) distribution.

In an alternative embodiment, the threshold is a function of the rate of fall off in the tail of a distribution. The rate of fall off may be measured by locating the ST deviation boundaries, as described above. If the histogram bins are labeled as [B1, B2 . . . BN], with B1 the lower boundary bin and BN the higher boundary bin, the difference in the number of elements between bins B1 and B2 is n(B2)−n(B1)=d(2,1), where d(a,b) is defined as the difference operator between bins a and b. Two measures of the rate of fall off of the lower tail of the distribution are: (1) max(d(i+1,i)) with i taken over the first p histogram bins; and (2) n(1:p)/n(total histogram), so that if the cumulative number of entries in the first p histograms is relatively large compared to the total number of entries in the histogram, the rate of fall toward the boundary is relatively sharper. An analogous rate of fall off is computed for the upper boundary.

In another alternative embodiment, if particular lead registers a normal QRS morphology, the positive threshold is never allowed to fall beneath a minimum value that is selected according to population based statistics. In yet another alternative embodiment, THP=STm+U*disp_pos*f(disp_pos), where f is a function that maps relatively low values of disppos to values greater than one, and maps relatively high values of disppos to values less than or equal to one, in such a manner that the detection thresholds for small and large dispersions are brought somewhat closer together. An inverted sigmoidal type shape for f is preferred. In this manner, the thresholds associated with small dispersions are relatively increased, which may help to avoid false positive detections that would otherwise result from very small dispersions.

Next, block 508 determines whether the ST deviation associated with the minimum bin is greater than a parameter Zeroth, which is a programmable parameter that governs the ST deviation level at which an ST deviation polarity change is deemed to occur, i.e. Zeroth is the boundary between positive and negative ST deviations. Zeroth will generally be 0, except that for some subjects, it may be desirable to set Zeroth as slightly negative since some random fluctuations in ST deviation can cause some negative (but small) ST deviations to accumulate in the ST histograms. Also, device related issues such as filtering could result in an offset to "true" ST deviations and thus result in a non-zero value for Zeroth.

If the ST level associated with minBin is greater than Zeroth, then block 510 provisionally sets the negative threshold analogously to the positive threshold setting described with reference to block 506. Programmable parameter L1 (block 510) may be set to a different value than programmable parameter U (block 506). In block 512, THN is not allowed to be greater than minTHul, a programmable parameter. THN is not allowed to be less than Zeroth less a margin of safety (NSF). For example, if Zeroth is 0, and NSF is 10, THN will be set no lower than −10. This floor on THN allows for greater sensitivity to detect changes in polarity. That is, if a negative ST deviation is not normal for a particular RR interval and lead, then the floor on THN allows a negative ST deviation to be detected with greater sensitivity if the provisional threshold set in block 510 is less than Zeroth-NSF.

On the other hand, if the provisional threshold set in block 510 is positive and "too large", then specificity may be compromised since small but positive ST deviations may be normal, even if not previously occurring in a particular subject. If the small ST deviations are associated with small QR amplitudes, then blocks 408 and 410 of FIG. 11 will prevent false positive detections. However, if the QR amplitude is not "small" but the ST deviation is small and positive, detection may still not be appropriate. The parameter minTHul dictates the level at which an ST deviation can not be considered as a true positive, regardless of ST/RR distributions. If a typical ST deviation distribution ranges between 400 and 1000, then minTHul is preferably set at 50 (relatively close to zero).

Returning to block 508, if ST(minbin) is less than or equal to Zeroth, then the negative threshold is set in block 514 analogously to block 506, with L2 being an individually set programmable parameter.

In the preferred embodiment, the parameters U, L1 and L2 (blocks 506, 510 and 514) change from relatively large values to lower values over time after the device 3 (FIG. 1) is first implanted.

In an alternative embodiment, U (block 506), L1 (block 510) and L2 (block 514) are heart rate dependent, so that the values of U, L1 and L2 increase with increasing heart rate.

FIGS. 14A-14F are an alternative embodiment of a process for setting ST deviation thresholds for detecting acute ischemic events. Block 600 is analogous to block 480 (FIG. 13A). Block 602 indicates the initiation of a loop through each RR interval range. This loop is indexed by the counter i. In block 606, the number of elements in the current RR interval bin (RR(i)) is compared to a threshold TH1bin. If the threshold is exceeded, control passes to block 608, which sets the threshold of bin i to the value determined by getbinTH (FIG. 13B). Next, in block 610, the number of elements in RR(i) is compared to another threshold, TH2bin, which greater than TH1bin. If TH2bin is exceeded, then the routine continues processing with the next RR interval, as indicated by the increment of i in block 612. Otherwise, if N(RR(i)) is less than TH2bin, then there is relatively less confidence in statistical estimates associated with RR(i), and the threshold is pushed further away from the median by an amount P, in block 614. Processing then continues in block 612.

Returning to block 606, if TH1bin is not exceeded, control passes to block 681m, which sets the threshold of the current bin equal to the threshold of previous bin (i−1). Processing then continues in block 612.

FIG. 15 is a table 700 that shows ischemia detection thresholds based on the combination of ST segment information from two leads, designated as the left and leftup leads respectively (leads 2 and 1 of FIG. 1). ST deviations of the leads are combined by effectively normalizing the individual leads' ST deviations to their corresponding thresholds. (Thresholds are assumed to be RR dependent but this need not be the case.) Column 702 of the table indicates the relative polarities of the ST shifts associated with the two leads. Column 704 shows the classifier that is generated to compare to a threshold shown in column 706.

The second row 708 in the table applies when the ST deviations of both the leads are above the pertinent (preferably RR dependent) median levels. The ST deviations are effectively normalized by subtracting the positive boundary ST deviation (STMX, which is label for the quantity ST(max-bin) described with reference to blocks 500 and 506 of FIG. 13B) and dividing the resulting quantity by the difference between the positive threshold and the positive boundary. For example, for the left lead, if the positive boundary STMX_left is 10, the positive threshold THP left is 20, and the ST deviation (ST_left) is 14, the effective normalized ST deviation is (14−10)/(20−10)=0.4.

Because the thresholds in column 706 are less than 2, ischemia may be detected when detection would not occur from either lead alone. Continuing with the above example for the left lead but adding in the leftup lead, if the positive boundary STMX_leftup is 14, the positive threshold THP_leftup is 30, and the ST deviation (ST_leftup) is 29, the effective normalized ST deviation for the leftup lead is (29−14)/(30−14)=0.9 (with integer based arithmetic). When the 0.9 for the leftup is added to the 0.4 of the left, the result is 1.3, the threshold for detection.

Combinations of ST deviations above and below the medians are shown in the remaining rows in the table 700.

In the preferred embodiment, it is desirable to base ischemia detection both on the relative "distance" classifiers described above but also on absolute "distance" from the boundary thresholds, as described in U.S. patent application Ser. No. 12/461,442, invented by Hopenfeld, filed August 2009. (The "absolute" distance may be either based in units of absolute voltage or be based on a fraction of QRS amplitude.) Ischemia is detected when any of the absolute or relative classifiers is above its corresponding threshold for a certain number of consecutive segments.

As is well known, integer based arithmetic, which is the preferred system for carrying out the operations described above, can produce undesirable results if the pertinent operands do not have sufficient granularity. For example, if 10 is divided by 6, the result is 1, compared to the desired result of 5/3. To reduce these types of problems, the data may be appropriate scaled. Continuing with the above example, if 10 is scaled up to 100 and then divided by 6, the result is 5, which (when divided by 10), is closer to the desired number 5/3. Appropriate scaling is performed to compare quantities that have been maintained at different scales. Continuing with the above example, if a threshold (to be applied to the value 10/6) is 2, it is scaled to 20, which may then be compared with the scaled value of 5.

For ease of understanding, the scaling factors (which are device and data dependent) have been omitted from the above description. The preferred scaling factors for various quantities are as follows. With regard to blocks 262 and 314 of FIGS. 7 and 9 respectively, mStDevNavg and MStDevN_xavg are both scaled by a factor of 5. With regard to FIG. 6B, ST_int and ST_ind-Rpeak_ind are scaled by a factor of 16 for purposes of computing the exponential average in block 236. Because integer based arithmetic results in rounding down of fractions, the quantity of ½ is added to compensate for bias that would otherwise result from such truncation. All QR related quantities are scaled by a factor of 128.

The invention claimed is:

1. A cardiac monitor comprising: (a) a sensor adapted to sense an analog signal from a heart; (b) a device coupled to the sensor, the device having an analog-to-digital circuit system contained therein for digitizing the analog signal to produce a digitized waveform; (c) a processor electrically coupled to the analog-to-digital circuit system, said processor configured to: (i) compute first and second pluralities of ST deviations from the digitized waveform over initial and subsequent time periods respectively, each of the pluralities of ST deviations being characterized by a statistical distribution; (ii) storing data pertaining to the first and second pluralities of ST deviations in a form that enables characteristics of the statistical distribution to be computed; (iii) form a first threshold that is based on the statistical distribution associated with the first plurality of ST deviations in said initial time period; (iv) apply a test to detect a cardiac event, wherein the test is based on the first threshold formed in said initial time interval; (v) form a second threshold that is based on the statistical distribution associated with the second plurality of ST deviations in a second time interval subsequent to said first time interval, wherein the second threshold in said second time interval is constrained by the value of the first threshold in said initial time interval; (vi) apply a test to detect a cardiac event, wherein the test is based on the second threshold of said second time interval.

2. The cardiac monitor of claim 1 wherein the second threshold is constrained by the value of the first threshold by determining the second threshold as an explicit function of the first detection threshold.

3. The cardiac monitor of claim 2 wherein the processor is further configured to form a provisional threshold based on the second plurality of ST deviations, and wherein the second threshold is an explicit function of the first threshold and the provisional threshold.

4. The cardiac monitor of claim 3 wherein the second threshold is a weighted average of the first threshold and the provisional threshold.

5. The cardiac monitor of claim 4 wherein the weighted average applies weights that increase with the number of ST deviations on which the first and provisional thresholds are based.

6. The cardiac monitor of claim 1 wherein the second threshold is based on the statistical distributions associated with both the first and second pluralities of ST deviations.

7. The cardiac monitor of claim 1 wherein said processor is further configured to store ST deviation according to heart rate ranges, and wherein the first and second pluralities of ST deviations correspond to a single heart rate range.

8. The cardiac monitor of claim 1 wherein the initial and subsequent time periods partially overlap.

9. The cardiac monitor of claim 1 wherein the processor is further configured to determine a boundary of the first statistical distribution, and wherein the first detection threshold is a function of the boundary.

* * * * *